(12) United States Patent
Morishima et al.

(10) Patent No.: US 10,045,693 B2
(45) Date of Patent: Aug. 14, 2018

(54) OPHTHALMOLOGIC OBSERVATION APPARATUS

(71) Applicant: KABUSHIKI KAISHA TOPCON, Tokyo (JP)

(72) Inventors: Ryuichi Morishima, Tokyo (JP); Kohta Fujii, Toda (JP)

(73) Assignee: KABUSHIKI KAISHA TOPCON, Tokyo (JP)

( * ) Notice: Subject to any disclaimer, the term of this patent is extended or adjusted under 35 U.S.C. 154(b) by 292 days.

(21) Appl. No.: 14/430,150

(22) PCT Filed: Sep. 12, 2013

(86) PCT No.: PCT/JP2013/074616
§ 371 (c)(1),
(2) Date: Mar. 20, 2015

(87) PCT Pub. No.: WO2014/054394
PCT Pub. Date: Apr. 10, 2014

(65) Prior Publication Data
US 2015/0223685 A1    Aug. 13, 2015

(30) Foreign Application Priority Data

Oct. 1, 2012    (JP) .................................. 2012-219152
Nov. 30, 2012   (JP) .................................. 2012-263203

(51) Int. Cl.
*A61B 3/12*    (2006.01)
*A61B 3/10*    (2006.01)
(Continued)

(52) U.S. Cl.
CPC .............. *A61B 3/12* (2013.01); *A61B 3/0025* (2013.01); *A61B 3/0041* (2013.01);
(Continued)

(58) Field of Classification Search
CPC ....... A61B 3/12; A61B 3/0025; A61B 3/0041; A61B 3/0058; A61B 3/0075; A61B 3/102; A61B 3/103; A61B 3/14; A61B 3/113
(Continued)

(56) References Cited

U.S. PATENT DOCUMENTS 5,596,377 A * 1/1997 Yano ...................... A61B 3/145
                                                       351/208
6,377,349 B1   4/2002 Fercher
(Continued)

FOREIGN PATENT DOCUMENTS

| CL | 200402942   | 3/2006  |
|----|-------------|---------|
| JP | 09-276232 A | 10/1997 |

(Continued)

OTHER PUBLICATIONS

International Searching Authority, "Written Opinion of the International Searching Authority", PCT/JP2013/074616, dated Oct. 15, 2013.*

(Continued)

*Primary Examiner* — William R Alexander
*Assistant Examiner* — Wen Huang
(74) *Attorney, Agent, or Firm* — Procopio, Cory, Hargreaves & Savitch LLP

(57) ABSTRACT

An ophthalmologic observation apparatus of an embodiment includes a photographing optical system, measuring optical system, optical-path coupler, first and second drivers and controller. The photographing optical system includes a first focusing lens and performs photography for acquiring a front image of an eye. The measuring optical system includes a second focusing lens and performs OCT for acquiring a cross-sectional image of the eye. The optical-path coupler couples optical paths of the photographing (Continued)

optical system and measuring optical system at a location on the eye side than the first and second focusing lenses. The first driver moves the first focusing lens along an optical axis of the photographing optical system. The second driver moves the second focusing lens along an optical axis of the measuring optical system. The controller controls the first and second drivers individually.

16 Claims, 12 Drawing Sheets

(51) Int. Cl.
*A61B 3/14* (2006.01)
*A61B 3/00* (2006.01)
*A61B 3/103* (2006.01)
*A61B 3/113* (2006.01)

(52) U.S. Cl.
CPC .......... *A61B 3/0058* (2013.01); *A61B 3/0075* (2013.01); *A61B 3/102* (2013.01); *A61B 3/103* (2013.01); *A61B 3/14* (2013.01); *A61B 3/113* (2013.01)

(58) Field of Classification Search
USPC ....................................................... 351/206
See application file for complete search history.

(56) References Cited

U.S. PATENT DOCUMENTS

| | | | |
|---|---|---|---|
| 2005/0074508 | A1 | 4/2005 | San Martin |
| 2006/0100528 | A1 | 5/2006 | Chan et al. |
| 2007/0196517 | A1 | 8/2007 | San Martin |
| 2007/0222945 | A1 | 9/2007 | Tsukada et al. |
| 2008/0226682 | A1 | 9/2008 | Brake et al. |
| 2009/0115964 | A1* | 5/2009 | Ueno .................... A61B 3/0058 351/206 |
| 2009/0244483 | A1 | 10/2009 | Yoshino et al. |
| 2009/0303438 | A1 | 12/2009 | Yamada et al. |
| 2010/0165291 | A1 | 7/2010 | Sugita et al. |

FOREIGN PATENT DOCUMENTS

| | | |
|---|---|---|
| JP | 11-325849 A | 11/1999 |
| JP | 2000116603 A | 4/2000 |
| JP | 2002-139421 A | 5/2002 |
| JP | 2006-153838 A | 6/2006 |
| JP | 2007-024677 A | 2/2007 |
| JP | 2007252693 A | 10/2007 |
| JP | 2008-073099 A | 4/2008 |
| JP | 2008-259544 A | 10/2008 |
| JP | 2009-011381 A | 1/2009 |
| JP | 2009240625 A | 10/2009 |
| JP | 2009-291252 A | 12/2009 |
| JP | 2009-291253 A | 12/2009 |
| JP | 2010136781 A | 6/2010 |
| JP | 2010-169660 A | 8/2010 |
| JP | 2011-245183 A | 12/2011 |
| WO | 0151083 A2 | 7/2001 |
| WO | 2014052378 A2 | 4/2014 |
| WO | 2015155293 A1 | 10/2015 |
| WO | 2015179840 A1 | 11/2015 |

OTHER PUBLICATIONS

Mitsuo, "Fundus Imaging Apparatus", JP2011-245183A, machine translation.*
International Search Report dated Oct. 2, 2013, issued for International Application No. PCT/JP2013/074616.
Tobar, Ivan, et al. "Successive Oral Immunizations against Piscirickettsia salmonis and Infectious Salmon Anemia Virus are Required to Maintain a Long-Term Protection in Farmed Salmonids", May 27, 2015. Frontiers in Immunology, (6) 244) DOI: 10.3389/fmmu.2015.00244 7 pages.
Tapia, D., et al. "Detection and Phylogenetic Analysis of Infectious Pancreatic Necrosis Virus in Chile" Oct. 27, 2015. Diseases of Aquatic Organisms, 116 (3), 173-184, 12 pages. DOI: 10.3354/dao02912.
Sernapesca (2013). Informe sanitario de salmonicultura en centros marinos 2012, Servicio Nacional de Pesca y Acuicultura. Valparaíso Government of Chile. 30 pages. Untranslated. www.sernapesca.cl.
Jensen, Brill Bang., et al. "Risk Factors for Outbreaks of Infectious Pancreatic Necrosis (IPN) and Associated Mortality in Norweigian Salmonid Farming", Diseases of Aquatic Organisms, 114 (3), 177-187 (2015). 11 pages.
Bragg, R.R., and Combrink, M.E., "Isolation and Identification of Infectious Pancreatic Necrosis (IPN) Virus From Rainbow Trout in South Africa", Doctoral Dissertation (2015) 3 pages. Bull. Eur. Ass. Fish Pathol. 7 95), 118, 1987.
Vike, Siri, et al. "Release and Survival of Infectious Salmon Anaemia (ISA) Virus During Decomposition of Atlantic Salmon (*Salmo salar* L.)" Copyright 2013 Elsevier B.V. Oct. 2, 2013. (2014). Aquaculture, 420, 119-125 7 pages.
Robledo, Diego, et al. "Gene Expression Comparison of Resistant and Susceptible Atlantic Salmon Fry Challenged with Infectious Pancreatic Necrosis Virus Reveals a Marked Contrast in Immune Response" (2016). BMC Genomics, 17 (1), 1). 16 pages. Copyright 2016 Rebledo et al. BioMed Central DOI 10.1 186/s 12864-016-2600-y.
Kousoulaki, Katerina, et al. "Metabolism, Health and Fillet Nutritional Quality in Atlantic Salmon (*Salmo salar*) Fed Diets Containing n-3-rich Microalgae" (2015). Journal of Nutritional Science, vol. 4, e24, pp. 1-13 DOI:10.1017/jns.2015.14 13 pages. Copyright the Author(s) 2015.
San Martin, Ricardo and Briones, Reinaldo "Industrial Uses and Sustainable Supply of Quillaja Saponaria (Rosaceae) Saponins" (1999). Economic Botany, 53 (3), 302-311) 10 pages. Copyright 1999 by the New York Botanical Garden Press, Bronx NY US.
San Martin, Ricardo and Briones, Reinaldo "Quality Control of Commercial Quillaja (*Quillaja saponaria molina*) Extracts by Reverse Phase HPLC" (2000). Journal of the Science of Food and Agriculture, 80 (14), 2063-2068). 6 pages. Copyright 2000 Society of Chemical Industry. J Sci Food Agric 0022-5142/2000.
Maier, Christiane, et al. "Phenolic Constituents in Commercial Aqueous Quillaja (*Quillaja saponaria molina*) Wood Extracts" Jan. 27, 2015. Journal of Agricultural and Food Chemistry, 63 (6), 1756-1762 7 pages. DOI: 10.1021/f506277p American Chemical Society.
Elizondo, Ernesto A. Moya, et al. "Evaluation of a Quillaja Saponaria Saponin Extract Fro Control of Powdery Mildew of Wheat and Squash" (2010). Agro south, vol. 38 (2), 87-96 10 pages.
Wang, Yujuan, et al., "Adjuvant Effect of Quillaja saponaria Saponin (QSS) on Protective Efficacy and IgM Generation in Turbot (*Scophthalmus maximus*) upon Immersion Vaccination" International Journal of Molecular Sciences, 2016, 17, 325; DOI: 10.3390/ijms17030325 13 pages.
Fernandes, Rosangela Do Nascimento, (2014) Use of Quillaia saponin (*Quillaja saponaria molina*) in Juveniles of Pacu, Universidade Estadual Paulista, Faculty of Agricultural Sciences and Veterinary Center Aqüicultura, Brazil PhD Thesis 115 pages. Untranslated. Jaboticabal, 2014 F363u CDU 639.3.043.
Vinay, Tharabenahalli-Nagaraju, et al. "Toxicity and Dose Determination of Quillaja Saponin, Aluminum Hydroxide and Squalene in Olive Flounder (*Paralichthys olivaceus*)" (2014), Veterinary immunology and immunopathology, 158 (1), 73-85 14 pages. Copyright 2013 Elsevier B.V. 0165-2427 http://dx.doi.org/10.1016/j.vetimm.2013.03.007.
Krogdahl, Ashild, et al. "Soya Saponins Induce Enteritis in Atlantic Salmon (*Salmo salar* L.)" Mar. 23, 2015, Journal of Agricultural and Food Chemistry 2015, 63, 3887-3902 16 pages. Copyright 2015 American Chemical Society DOI: 10.1021/jf506242t.

(56) References Cited

OTHER PUBLICATIONS

Francis, George, et al., "Effects of Long Term Feeding of Quillaja saponins on sex ratio, muscle and serum cholesterol and LH levels in Nile tilapia (*Oreochromis niloticus* (L))." Comparative Biochemistry and Physiology Part C: Toxicology & Pharmacology 133.4 (2002): 593-603. 11 pages. 1532-0456/02 Copyright 2002 Elsevier Science Inc. PII: S1532-0456(02)00167-9.

Diagnostic Manual for Aquatic Animal Diseases, 3rd edn. OIE, Paris 2000 281 pages. ISBN 92-9044-538-6 copyright 2000 Office International des Epizooties.

Office Action for Japanese Patent Application No. 2016-171970 dated Jul. 4, 2017. 4 pages.

\* cited by examiner

OPHTHALMOLOGIC OBSERVATION APPARATUS

The present application is a National Stage entry of PCT/JP2013/074616, filed on Sep. 12, 2013, which claims priority from Japanese Patent Application Nos. 2012-219152, filed Oct. 1, 2012, and 2012-263203, filed Nov. 20, 2012, the contents of which are incorporated herein by reference in their entirety.

TECHNICAL FIELD

The present invention relates to an ophthalmologic observation apparatus that acquires images of an eye.

BACKGROUND TECHNOLOGY

In recent years, optical coherence tomography (OCT) for forming images that represent surface and/or internal morphologies of objects by using light beams from laser light sources etc. has attracted attention. Unlike X-ray CT, optical coherence tomography is noninvasive to human bodies and is therefore expected to be utilized in medical and biological fields in particular. For example, in ophthalmology, apparatuses for forming images of fundus, cornea, etc. are in practical stages.

An apparatus disclosed in Patent Document 1 uses so-called "Fourier Domain OCT" technique. More specifically, this apparatus irradiates low-coherence light beam to an object, superposes its reflected light and reference light to generate interference light, and acquires spectral intensity distribution of the interference light and executes Fourier transform to image morphology in a depth direction (z-direction) of the object. Further, this apparatus is provided with a galvano mirror for scanning light beams (signal light) along one direction (x-direction) perpendicular to the z-direction, and forms an image of a desired measurement target region of the object. An image formed by this apparatus is a two-dimensional cross-sectional image along the depth direction (z-direction) and scanning direction (x-direction) of the light beam. Such a technique is specifically called Spectral Domain.

Patent Document 2 discloses a technique that scans signal light in horizontal and vertical directions (x-direction and y-direction) to form two-dimensional cross-sectional images along the horizontal direction, and acquires three-dimensional cross-sectional information of a measured area based on these cross-sectional images to perform imaging. Such three-dimensional imaging techniques include, for example, a method that arranges and displays cross-sectional images along the vertical direction (referred to as stack data etc.), method that executing rendering processing on volume data (voxel data) created from stack data to form a three-dimensional image.

Patent Documents 3 and 4 disclose other types of OCT. An OCT apparatus disclosed in Patent Document 3 scans wavelengths of light irradiated to an object (wavelength sweeping), detects interference light obtained by superposing reflected lights of the respective wavelengths on reference light to acquire spectral intensity distribution, and executes Fourier transform on it to image morphology of an object. Such an OCT technique is called Swept Source etc. Swept Source OCT is a kind of Fourier Domain OCT.

An OCT apparatus disclosed in Patent Document 4 irradiates light having predetermined beam diameter to an object and analyzes components of interference light obtained by superposing reflected light thereof and reference light, thereby forming an image of a cross section of the object orthogonal to irradiating direction of the light. Such an OCT technique is called Full-Field, En-face, etc.

Patent Document 5 discloses an example of OCT application to ophthalmology. Before OCT was applied, retinal cameras, slit lamp microscopes, scanning laser ophthalmoscopes (SLO) etc. were used for observing eyes (see Patent Documents 6 to 8 for example). Retinal cameras photograph fundus by irradiating illumination light onto an eye and receiving reflected light from the fundus. Slit lamp microscopes obtain a cross-sectional image of cornea by cutting off a light section of the cornea using slit light. SLO images morphology of retinal surface by scanning fundus with laser light and detecting reflected light by high-sensitive elements such as a photomultiplier. These modalities photograph fundus, cornea, etc. from the front to acquire images (front images).

OCT apparatuses have advantages over retinal cameras etc. in that high-definition images may be obtained, cross-sectional and three-dimensional images may be obtained, etc.

Because OCT apparatuses may be used for observing various sites of eyes and is capable of obtaining high-definition images in this way, they have been applied to diagnoses of various ophthalmologic disorders.

PRIOR ART DOCUMENTS

Patent Documents

[Patent Document 1] Japanese Unexamined Patent Application Publication No. H11-325849
[Patent Document 2] Japanese Unexamined Patent Application Publication No. 2002-139421
[Patent Document 3] Japanese Unexamined Patent Application Publication No. 2007-24677
[Patent Document 4] Japanese Unexamined Patent Application Publication No. 2006-153838
[Patent Document 5] Japanese Unexamined Patent Application Publication No. 2008-73099
[Patent Document 6] Japanese Unexamined Patent Application Publication No. H09-276232
[Patent Document 7] Japanese Unexamined Patent Application Publication No. 2008-259544
[Patent Document 8] Japanese Unexamined Patent Application Publication No. 2009-11381

SUMMARY OF THE INVENTION

Problems to be Solved by the Invention

As with the apparatus disclosed in Patent Document 5 for example, in conventional ophthalmologic observation apparatuses that can acquire both front images and OCT images, optical system for acquiring front images and optical system for OCT share a common focusing lens (lenses).

However, because light wavelengths for front-image acquisition (such as visible light) and light wavelengths for OCT (such as near-infrared light) are different from each other, optimal focus positions for these modalities are different.

Means for Solving the Problem

An embodiment is an ophthalmologic observation apparatus comprising: a photographing optical system that includes a first focusing lens and performs photography for acquiring a front image of an eye; a measuring optical system that includes a second focusing lens and performs optical coherence tomography (OCT) for acquiring a cross-sectional image of the eye; an optical-path coupler that couples optical paths of the photographing optical system and the measuring optical system at a location on the eye side than the first and second focusing lenses; a first driver for moving the first focusing lens along an optical axis of the photographing optical system; a second driver for moving the second focusing lens along an optical axis of the measuring optical system; and a controller that controls the first and second drivers individually.

The invention described in claim 3 is the ophthalmologic observation apparatus of claim 2, wherein the photographing optical system includes an infrared photographing optical system that uses infrared light to perform photography of the fundus, and the refractive-power obtaining part includes: a projecting optical system that projects, onto the fundus, a focusing index indicating a state of focus of the photographing optical system on the fundus; and an analyzer that analyzes a front image acquired by photographing the fundus on which the focusing index is projected by means of the infrared photographing optical system to obtain refractive power of the eye.

The invention described in claim 4 is the ophthalmologic observation apparatus of claim 2 or 3, wherein the controller includes a storage that stores in advance: first association information in which values of eye refractive power and positions of the first focusing lens are associated; and second association information in which values of eye refractive power and positions of the second focusing lens are associated, and the first target-position obtaining part obtains target positions of the first and second focusing lenses based on the refractive power obtained by the refractive-power obtaining part and the first and second association information.

The invention described in claim 16 is the ophthalmologic observation apparatus of claim 15, wherein the predetermined range includes a position of the second focusing lens determined based on the focusing index in advance.

Effect of the Invention

According to the present invention, it is possible to perform both front-image acquisition and OCT of an eye with suitable focus conditions.

MODE FOR CARRYING OUT THE INVENTION

Examples of embodiments of ophthalmological imaging apparatuses are described in detail with reference to drawings. Ophthalmologic observation apparatuses according to embodiments have a function that uses OCT to acquire cross-sectional images and/or three-dimensional images of an eye (fundus, anterior eye part, etc.) and a function that photographs the eye to acquire front images. In this specification, images acquired by OCT are sometimes referred to as OCT images. Further, a measurement operation for forming OCT images is sometimes referred to as OCT (measurement). The contents disclosed in the documents cited in this specification may be applied to the following embodiments.

In the following embodiments, configurations in which Fourier Domain OCT is employed are described in detail. Particularly, ophthalmologic observation apparatuses described later are capable of obtaining OCT image by means of Spectral Domain OCT as the apparatus disclosed in Patent Document 5. Configurations according to the present invention may be applied to ophthalmologic observation apparatuses of any type other than Spectral Domain (for example, Swept Source OCT). The following embodiments describe apparatuses as a combination of OCT apparatus and retinal camera; however, an ophthalmologic photographing apparatus other than a retinal camera such as SLO, slit lamp microscope, ophthalmologic operation microscope, etc. may be combined with an OCT apparatus.

First Embodiment

[Configurations]

Figure 1:
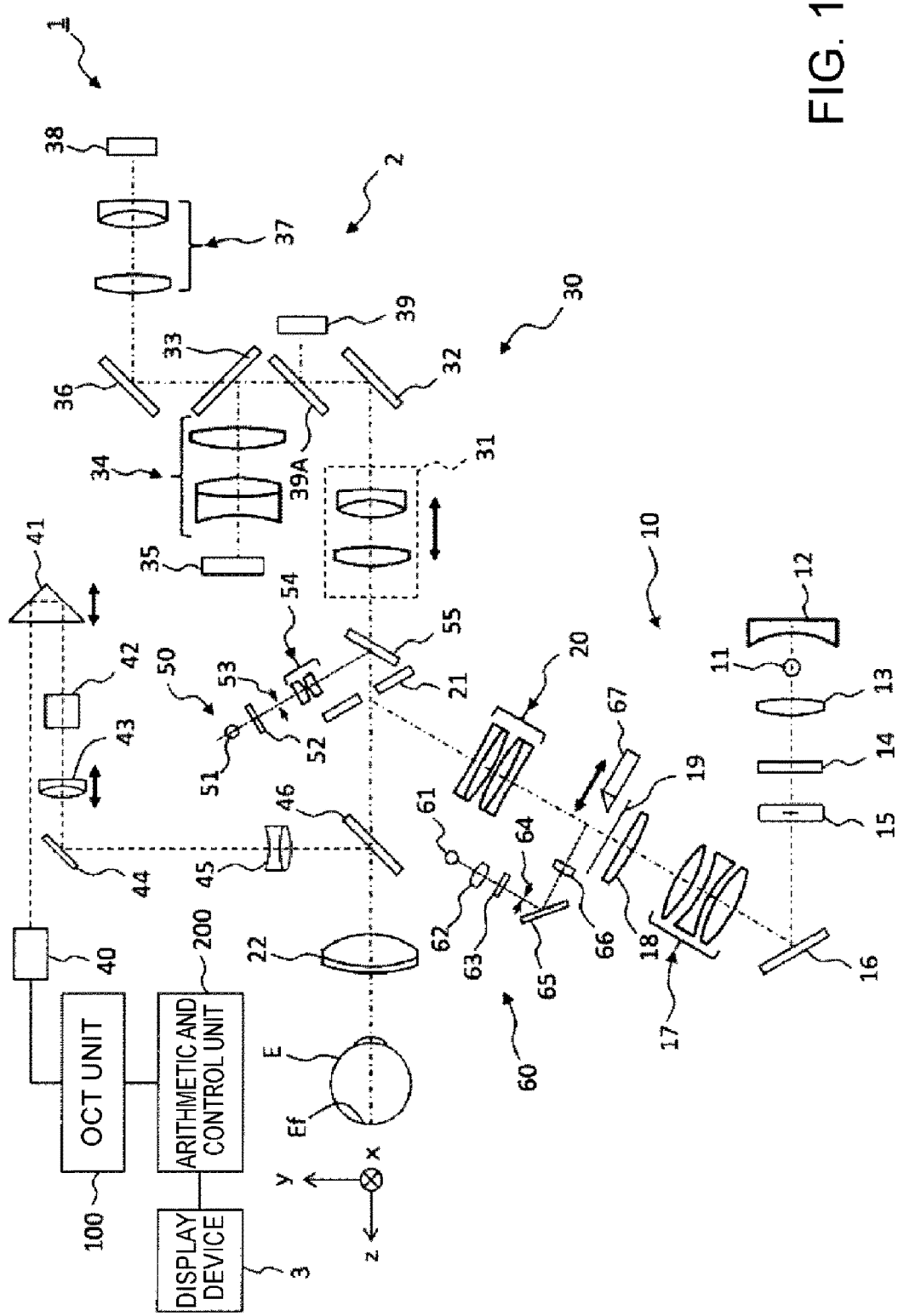
FIG. 1 is a schematic diagram illustrating a configuration example of an ophthalmologic observation apparatus according to an embodiment.
Figure 2:
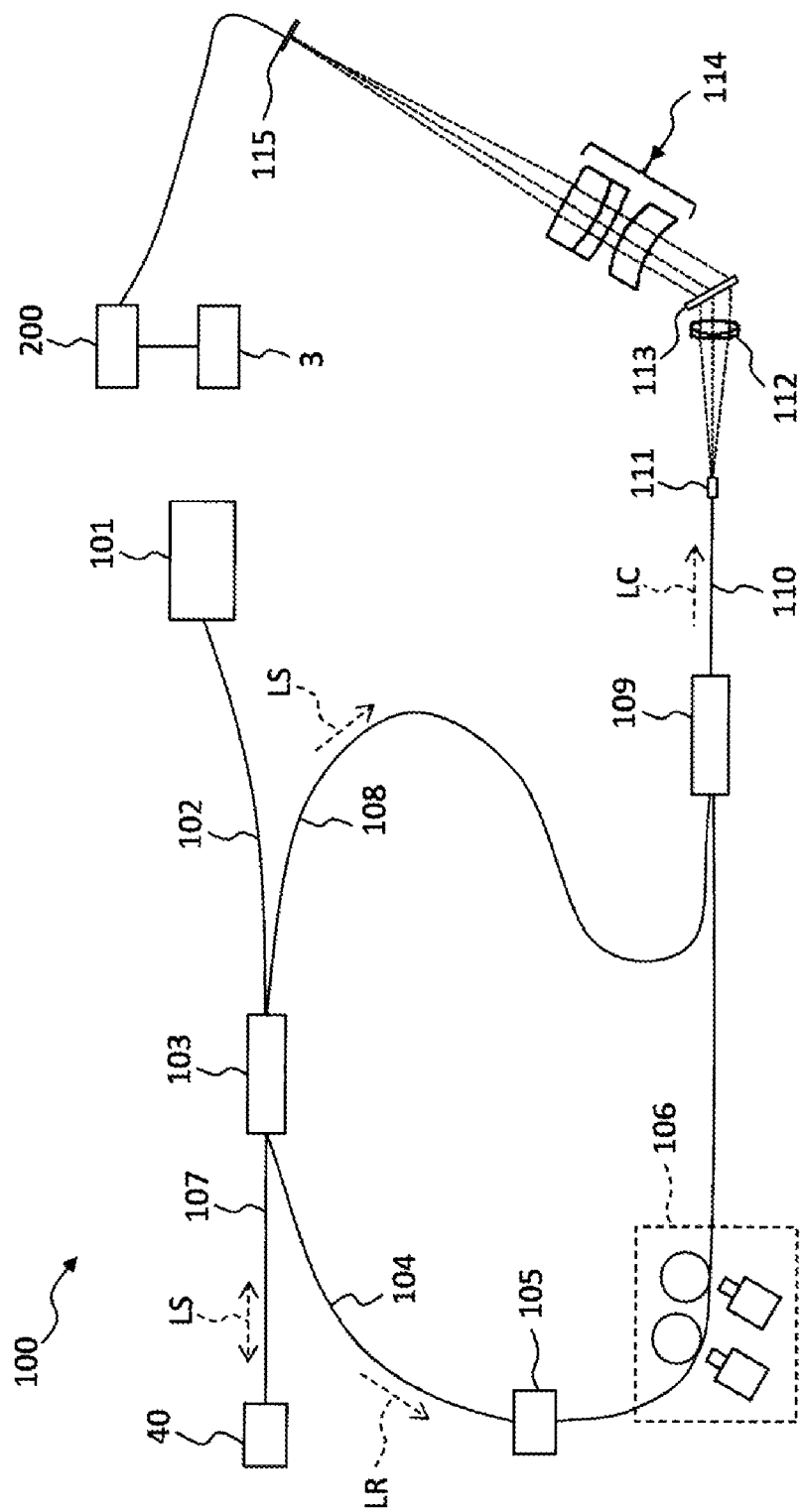
FIG. 2 is a schematic diagram illustrating a configuration example of an ophthalmologic observation apparatus according to an embodiment.

An ophthalmologic observation apparatus 1, as shown in FIG. 1 and FIG. 2, includes a retinal camera unit 2, OCT unit 100 and arithmetic and control unit 200. The retinal camera unit 2 includes almost the same optical system as a conventional retinal camera. The OCT unit 100 is provided with an optical system for obtaining fundus OCT images. The arithmetic and control unit 200 includes a computer that executes various arithmetic processing, control processing, etc.

[Retinal Camera Unit]

The retinal camera unit 2 shown in FIG. 1 is provided with an optical system for obtaining front images (fundus images) representing surface morphology of a fundus Ef of an eye E. Fundus images include observation images, photographed images, etc. The observation image is, for example, a monochromatic moving image formed at a predetermined frame rate using near-infrared light. The photographed image may be, for example, a color image captured by flashing visible light or a monochromatic still image captured by using near-infrared light or visible light as illumination light. The retinal camera unit 2 may also capture other types of images such as fluorescein angiography images, indocyanine green fluorescent images and autofluorescent images.

The retinal camera unit 2 is provided with a chin rest and forehead placement for supporting a subject's face. Moreover, the retinal camera unit 2 is provided with an illumination optical system 10 and imaging optical system 30. The illumination optical system 10 irradiates illumination light to the fundus Ef. The imaging optical system 30 guides fundus-reflected light of illumination light to imaging devices (CCD image sensors 35, 38 (sometimes referred to simply as CCD)). The illumination optical system 10 and imaging optical system 30 function as an example of a "photographing optical system".

An observation light source 11 of the illumination optical system 10 includes a halogen lamp, for example. Light (observation illumination light) output from the observation light source 11 is reflected by a reflection mirror 12 with a curved reflection surface, passes through a condenser lens 13 and becomes near-infrared light after passing through a visible cut filter 14. Further, the observation illumination light is once converged near an imaging light source 15, reflected by a mirror 16 and passes through relay lenses 17 and 18, diaphragm 19 and relay lens 20. Then, the observation illumination light is reflected on a peripheral part (region surrounding an aperture part) of an aperture mirror 21, transmitted through a dichroic mirror 46 and refracted by an objective lens 22, thereby illuminating the fundus Ef. LED (Light Emitting Diode) may be used as the observation light source.

The fundus-reflected light of the observation illumination light is refracted by the objective lens 22, transmitted through the dichroic mirror 46, passes through the aperture part formed in the center region of the aperture mirror 21, transmitted through a dichroic mirror 55, travels through a focusing lens 31 and reflected by a mirror 32. Further, the fundus-reflected light is transmitted through a half-mirror 39A, reflected by a dichroic mirror 33 and forms an image on a light-receiving surface of the CCD 35 by a condenser lens 34. The CCD 35 detects the fundus-reflected light at a preset frame rate, for example. An image (observation image) based on the fundus-reflected light detected by the CCD 35 is displayed on a display device 3. When the imaging optical system 30 is focused on the anterior eye part, the observation image of the anterior eye part of the eye E is displayed. The optical system described above that illuminates the eye E with the observation illumination light and detects its reflected light is an example of an infrared photographing optical system.

The imaging light source 15 includes a xenon lamp, for example. Light (imaging illumination light) output from the imaging light source 15 is irradiated to the fundus Ef through the same route as the observation illumination light. The fundus-reflected light of the imaging illumination light is guided to the dichroic mirror 33 via the same route as the observation illumination light, transmitted through the dichroic mirror 33, reflected by a mirror 36 and forms an image on the light-receiving surface of the CCD 38 by a condenser lens 37. An image (photographed image) based on the fundus-reflected light detected by the CCD 38 is displayed on the display device 3. The display device 3 for displaying observation image and display device 3 for displaying photographed image may be the same or different. When similar photography is carried out by illuminating the eye E with infrared light, infrared photographed image is displayed. LED may be used as the imaging light source.

An LCD (Liquid Crystal Display) 39 displays fixation targets, targets for visual-acuity measurement, etc. The fixation target is a visual target (index) for fixating the eye E and used in fundus photography, OCT, etc.

Part of light output from the LCD 39 is reflected by the half-mirror 39A, reflected by the mirror 32, travels through the focusing lens 31 and dichroic mirror 55, passes through the aperture part of the aperture mirror 21, transmitted through the dichroic mirror 46, refracted by the objective lens 22, and projected onto the fundus Ef.

By changing a display position of the fixation target on the LCD 39's screen, a fixation position of the eye E may be changed. Examples of fixation positions of the eye E include position for acquiring a macula-centered image, position for acquiring optic-papilla-centered image, position for acquiring fundus-center image (centered at a location between macula and optic papilla), etc., as in conventional retinal cameras. Display positions of fixation targets may be changed arbitrarily.

As with conventional retinal cameras, the retinal camera unit 2 includes an alignment optical system 50 and focus optical system 60. The alignment optical system 50 generates a target (index, alignment target) for matching the position of the optical system to the eye E (that is, for performing alignment). The focus optical system 60 generates a target (index, split target) for adjusting focus on the eye Ef.

Light (alignment light) output from an LED 51 of the alignment optical system 50 passes through diaphragms 52 and 53 and relay lens 54, is reflected by the dichroic mirror 55, passes through the aperture part of the aperture mirror 21, is transmitted through the dichroic mirror 46 and is projected on the cornea of the eye E by the objective lens 22.

Cornea-reflected light of the alignment light passes through the objective lens 22, dichroic mirror 46 and aperture part, and then part of the cornea-reflected light is transmitted through the dichroic mirror 55, passes through the focusing lens 31, reflected by the mirror 32, transmitted through the half-mirror 39A, reflected by the dichroic mirror 33, and projected on the light-receiving surface of the CCD 35 by the condenser lens 34. An image (alignment target, alignment index) captured by the CCD 35 is displayed on the display device 3 together with observation image. The user conducts alignment by performing operations as with conventional retinal cameras. Alignment may be performed in a way in which the arithmetic and control unit 200 analyzes position of alignment target and moves the optical system (automatic alignment).

In order to perform focus adjustment, reflection surface of a reflection rod 67 is obliquely disposed in an optical path of the illumination optical system 10. Light (focus light) output from an LED 61 of the focus optical system 60 passes through a relay lens 62, is split into two light fluxes by a split target plate 63, passes through a two-hole diaphragm 64, is reflected by a mirror 65, is formed an image on the reflection surface of the reflection rod 67 by a condenser lens 66 and then is reflected. Further, the focus light passes through the relay lens 20, is reflected at the aperture mirror 21, is transmitted through the dichroic mirror 46, is refracted by the objective lens 22 and is projected on the fundus Ef.

Fundus-reflected light of the focus light passes through the same route as the cornea-reflected light of the alignment light and is detected by the CCD 35. An image (split target, split index) captured by the CCD 35 is displayed on the display device 3 together with observation image. The arithmetic and control unit 200, as in conventional technology, analyzes position of the split target and moves the focusing lens 31 and focus optical system 60 to execute focusing (automatic focusing). Focusing may be performed manually while observing split target.

The dichroic mirror 46 couples optical path for fundus photography and optical path for OCT. The dichroic mirror 46 reflects light of wavelength bands for OCT and transmits the light for fundus photography. The dichroic mirror 46 is an example of an optical-path coupler. The OCT optical path includes a collimator lens unit 40, optical-path-length changing part 41, galvano scanner 42, focusing lens 43, mirror 44 and relay lens 45. The optical system forming OCT optical path and optical system included in the OCT unit 100 is an example of a measuring optical system.

The optical-path-length changing part 41 is movable in the direction indicated by an arrow in FIG. 1 to change length of the OCT optical path. The change of optical path length may be used for correcting optical path length in accordance with axial length of the eye E, adjusting interference state, etc. The optic al-path-length changing part 41 includes a corner cube and mechanism for moving the corner cube, for example.

The galvano scanner 42 changes travelling direction of light (signal light LS) guided along the OCT optical path. Accordingly, the fundus Ef is scanned by the signal light LS. The galvano scanner 42 includes a galvano mirror for x-direction scanning of signal light LS, galvano mirror for y-direction scanning, and mechanism for independently driving these. Thereby, the signal light LS may be scanned in an arbitrary direction in the xy-plane.

[OCT Unit]

An example of the configuration of the OCT unit 100 is explained while referring to FIG. 2. The OCT unit 100 is provided with an optical system for obtaining OCT images of the fundus Ef. This optical system includes a configuration similar to conventional Spectral Domain OCT apparatus. That is, this optical system is configured to split low-coherence light into signal light and reference light, superpose the signal light returned form the fundus Ef with the reference light having traveled through a reference optical path to generate interference light, and detect spectral components of the interference light. The result of the detection (detection signal) is transmitted to the arithmetic and control unit 200.

When Swept Source OCT is applied, a wavelength-sweeping light source is provided instead of low-coherence light source while an optical member for spectrally decomposing interference light is not provided. In general, any known technology in accordance with OCT type may be arbitrarily applied for a configuration of the OCT unit 100.

A light source unit 101 outputs broadband low-coherence light L0. The low-coherence light L0, for example, contains near-infrared wavelength band (about 800-900 nm) and has temporal coherence length of about tens of micrometer. It is possible to use wavelength bands invisible for human eyes such as near-infrared light having center wavelength of about 1040-1060 nm as the low-coherence light L0.

The light source unit 101 includes light-emitting device, such as SLD (super luminescent diode), LED, SOA (Semiconductor Optical Amplifier), etc.

The low-coherence light L0 output from the light source unit 101 is guided to a fiber coupler 103 through an optical fiber 102 and split into signal light LS and reference light LR.

The reference light LR is guided to an optical attenuator 105 through an optical fiber 104. Using any known technology, the arithmetic and control unit 200 controls the optical attenuator 105 for automatically adjusting light quantity (light intensity) of the reference light LR guided through the optical fiber 104. The reference light LR whose light quantity has been adjusted by the optical attenuator 105 is guided through the optical fiber 104 and reaches a polarization controller 106. The polarization controller 106 applies stress from outside to the optical fiber 104 of loop-form to adjust polarization states of the reference light LR being guided in the optical fiber 104, for example. Configuration of the polarization controller 106 is not limited to this and arbitrary known technology may be applied. The reference light LR whose polarization state has been adjusted by the polarization controller 106 is guided to an optical coupler 109.

The signal light LS generated by the fiber coupler 103 is guided through the optical fiber 107 and converted into a parallel light flux by the collimator lens unit 40. Further, the signal light LS travels through the optical-path-length changing part 41, galvano scanner 42, focusing lens 43, mirror 44 and relay lens 45, and reaches the dichroic mirror 46. Further, the signal light LS is reflected by the dichroic mirror 46, refracted by the objective lens 22 and projected onto the fundus Ef. The signal light LS is scattered (reflected) at various depth positions of the fundus Ef. Backscattered light of the signal light LS from the fundus Ef travels along the same route as the outward way in the opposite direction to the fiber coupler 103, and reaches the fiber coupler 109 through an optical fiber 108.

The fiber coupler 109 superposes the back-scattered light of the signal light LS and the reference light LR having passed through the optical fiber 104. Interference light LC thus generated is guided by an optical fiber 110 and output from an exit end 111. Further, the interference light LC is converted into a parallel light flux by a collimator lens 112, spectrally divided (spectrally decomposed) by a diffraction grating 113, converged by a condenser lens 114, and projected onto light-receiving surface of a CCD (image sensor) 115. Although the diffraction grating 113 shown in FIG. 2 is of transmission type, any other kinds of spectrally decomposing elements (such as reflection type) may be used.

The CCD 115 is for example a line sensor, detects the respective spectral components of spectrally-decomposed interference light LC and converts the components into electric charges. The CCD 115 accumulates the electric charges, generates detection signals and transmits the detection signals to the arithmetic and control unit 200.

Although Michelson-type interferometer is employed in the embodiment, any type of interferometer such as a Mach-Zehnder-type may be employed as necessary. Instead of CCD, other types of image sensors such as CMOS (Complementary Metal Oxide Semiconductor) may be used.

[Arithmetic and Control Unit]

A configuration of the arithmetic and control unit 200 is described. The arithmetic and control unit 200 analyzes detection signals input from the CCD 115 to form OCT images of the fundus Ef. Arithmetic processing for this may be the same as conventional Spectral Domain OCT apparatus.

The arithmetic and control unit 200 controls each part of the retinal camera unit 2, display device 3 and OCT unit 100. For example, the arithmetic and control unit 200 displays OCT images of the fundus Ef on the display device 3.

As controls of the retinal camera unit 2, the arithmetic and control unit 200 executes: action controls of the observation light source 101, imaging light source 103 and LED's 51 and 61; action control of the LCD 39; movement controls of the focusing lenses 31 and 43; movement control of the reflection rod 67; movement control of the focus optical system 60; movement control of the optical-path-length changing part 41; action control of the galvano scanner 42; etc.

As controls of the OCT unit 100, the arithmetic and control unit 200 executes: action control of the light source unit 101; action control of the optical attenuator 105; action control of the polarization controller 106; action control of the CCD 115; etc.

The arithmetic and control unit 200 includes a microprocessor, RAM, ROM, hard disk drive, communication interface, etc. as with conventional computers. Storage devices such as hard disk drive store computer programs for controlling the ophthalmologic observation apparatus 1. The arithmetic and control unit 200 may include various circuit boards such as circuit boards for OCT-image formation. The arithmetic and control unit 200 may include operation devices (input devices) such as a keyboard, mouse and/or display device such as LCD.

The retinal camera unit 2, display device 3, OCT unit 100 and arithmetic and control unit 200 may be integrally configured (that is, provided within a single case) or separately configured in two or more cases.

[Control System]

Figure 3:
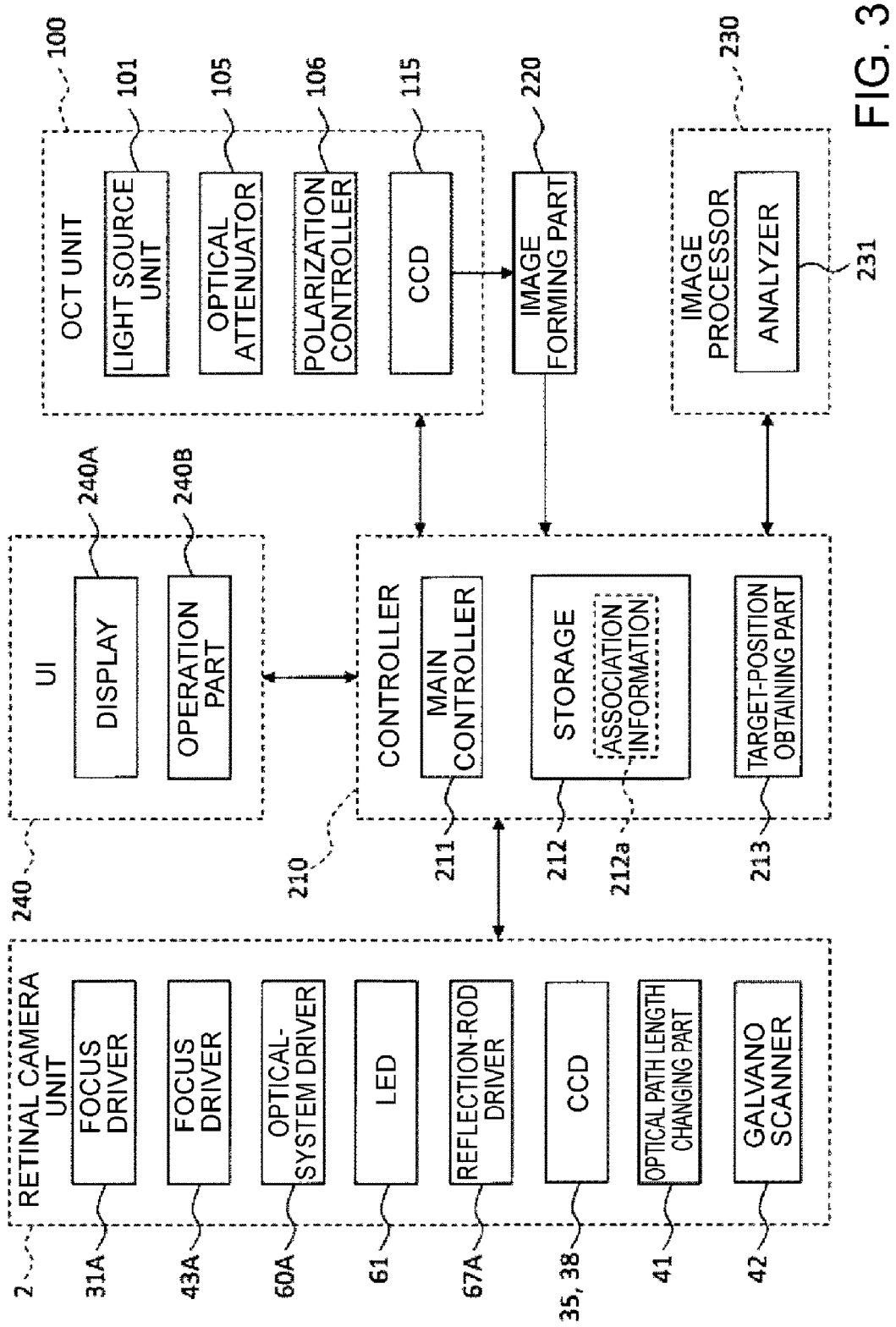
FIG. 3 is a schematic block diagram illustrating a configuration example of an ophthalmologic observation apparatus according to an embodiment.

A configuration of a control system of the ophthalmologic observation apparatus 1 is described with reference to FIG. 3.

(Controller)

A controller 210 is the center of the control system of the ophthalmologic observation apparatus 1. The controller 210 includes the above microprocessor, RAM, ROM, hard disk drive and communication interface, etc., for example. The controller 210 includes a main controller 211, storage 212 and target-position obtaining part 213.

(Main Controller)

The main controller 211 performs various controls as described above. Specifically, the main controller 211 controls focus drivers 31A and 43A, optical-system driver 60A, LED 61, reflection-rod driver 67A, CCD 35 and 38, optical-path-length changing part 41 and galvano scanner 42 in the retinal camera unit 2. Also, the main controller 211 controls the light source unit 101, optical attenuator 105, polarization controller 106 and CCD 115 in the OCT unit 100.

The focus driver 31A receives control from the main controller 211 and moves the focusing lens 31 along optical axis. Accordingly, focus position of the imaging optical system 30 is varied. The focus driver 31A includes an actuator such as a pulse motor and mechanism that transmits driving power generated by this actuator to the focusing lens 31. The focusing lens 31 is an example of a first focusing lens. The focus driver 31A is an example of a first driver.

The focus driver 43A receives control from the main controller 211 and moves the focusing lens 43 along optical axis. Accordingly, focus position of the measuring optical system for OCT is varied. Focus position of the measuring optical system regulates light quantity of signal light LS entering the optical fiber 107 via the collimator lens unit 40. Optimal focus position of the measuring optical system is realized by disposing the focusing lens 43 at a position at which the fiber end of the optical fiber 107 on the collimator lens unit 40 side and the fundus Ef are optically conjugate. The focus driver 43A includes an actuator such as a pulse motor and mechanism that transmits driving power generated by this actuator to the focusing lens 43.

The optical-system driver 60A receives control from the main controller 211 and moves the focus optical system 60 along optical axis. Accordingly, aspect of split target projected on the fundus Ef is varied. The optical-system driver 60A includes an actuator such as a pulse motor and mechanism that transmits driving power generated by this actuator to the focus optical system 60. The focus optical system 60 is configured as a unit, for example. The focus optical system 60 projects split target (focusing index) indicating a state of focus of the imaging optical system 30 on the fundus Ef and is an example of a projecting optical system.

The reflection-rod driver 67A receives control from the main controller 211 and inserts/removes the reflection rod 67 into/from optical path. The reflection rod 67 is inserted into the optical path when projecting split target (that is, at the commencement of focus adjustment) and removed from the optical path at the termination of focus adjustment. The reflection-rod driver 67A includes an actuator such as a solenoid and mechanism that transmits driving power generated by this actuator to the reflection rod 67.

The main controller 211 controls a driving mechanism (illustration omitted) to three-dimensionally move the retinal camera unit 2. Such control is used for alignment and tracking. Tracking is an operation for moving optical system in accordance with eye movement of the eye E. When tracking is performed, alignment and focusing are performed in advance. Tracking is a function to maintain adequate positional relationship in which alignment and focusing are matched by causing position of optical system to follow eye movement.

The main controller 211 executes processing of writing data into the storage 212 and processing of reading out data from the storage 212.

(Storage)

The storage 212 stores various kinds of data. Data stored in the storage 212 may include OCT image data, fundus image data, eye information, etc., for example. The eye information includes information on subjects such as patient ID's, names and information on eyes such as identification of left/right eye. The storage 212 stores various programs and data for operating the ophthalmologic observation apparatus 1.

Association information 212a is stored in the storage 212 of the present embodiment in advance. The association information 212a includes: first association information in which values of eye refractive power (diopters) and positions of the focusing lens 31 are associated with each other; and second association information in which values of eye refractive power (diopters) and positions of the focusing lens 43 are associated with each other. The first and second association information may be separated or unified. The association information 212a may be information in which discrete values are associated with each other such as a table or information in which continuous values are associated with each other such as a graph.

(Target-Position Obtaining Part)

The target-position obtaining part 213 obtains target positions of the respective focusing lenses 31 and 43 based on refractive power of the eye E. The target-position obtaining part 213 is an example of a first target-position obtaining part.

A target position is positional information treated as a destination of the focusing lens 31 (or 43). Such positional information indicates a position on the optical axis of the optical system in which the focusing lens 31 (or 43) is provided. The positional information may be information of any form. For example, the positional information may indicate a position on the optical axis itself or indicate contents of control signals for moving the focusing lens 31 (or 43) (such as the number of pulse signals transmitted to a pulse motor).

Refractive power of the eye E is obtained by any refractive-power obtaining part. For example, if refractive power of the eye E was measured in the past, a refractive-power obtaining part (such as the controller 210) may be configured to read out the value of the refractive power recorded in electric medical records. Alternatively, although detailed description is given later, an analyzer 231 in an image processor 230 may obtain refractive power of the eye E.

The target-position obtaining part 213 obtains target positions of the first and second focusing lenses 31 and 43 based on the refractive power obtained by the refractive-power obtaining part and association information 212a. More specifically, the target-position obtaining part 213 refers to the first association information to obtain a position of the focusing lens 31 corresponding to the value of refractive power obtained by the refractive-power obtaining part, and sets it to be a target position of the focusing lens 31. Similarly, the target-position obtaining part 213 refers to the second association information to obtain a position of the focusing lens 43 corresponding to the value of refractive power obtained by the refractive-power obtaining part, and sets it to be a target position of the focusing lens 43.

(Image Forming Part)

An image forming part 220 forms cross-sectional image data of the fundus Ef based on detection signals from the CCD 115. Like conventional Spectral Domain OCT, this processing includes noise elimination (noise reduction), filtering, dispersion compensation, FFT (Fast Fourier Transform), etc. For OCT apparatuses of other types, the image forming part 220 executes known processing in accordance with an applied type.

The image forming part 220 may include the aforementioned circuit boards, for example. "Image data" and an "image" based on this image data may be identified with each other in this specification.

(Image Processor)

An image processor 230 executes various image processing and analysis on images formed by the image forming part 220. For example, the image processor 230 executes various corrections such as brightness correction of images etc. Moreover, the image processor 230 executes various image processing and analysis on images obtained by the retinal camera unit 2 (fundus images, anterior eye part images, etc.).

The image processor 230 executes known image processing such as interpolation that interpolates pixels between cross-sectional images to form three-dimensional image data of the fundus Ef. Three-dimensional image data refers to image data whose pixel positions are defined by a three-dimensional coordinate system. Three-dimensional image data may be image data composed of three-dimensionally arranged voxels, for example. Such image data is referred to as volume data, voxel data, etc. For displaying an image based on volume data, the image processor 230 executes rendering processing (such as volume rendering, MIP (Maximum Intensity Projection), etc.) on the volume data to form image data of a pseudo three-dimensional image taken from a specific view direction. This pseudo three-dimensional image is displayed on a display 240A.

It is also possible to form stack data of cross-sectional images as three-dimensional image data. Stack data is image data obtained by three-dimensionally arranging cross-sectional images acquired along scanning lines, wherein the arrangement is based on positional relationship of the scanning lines. That is, stack data is image data obtained by representing, with a three-dimensional coordinate system, cross-sectional images originally defined in respective two-dimensional coordinate systems (in other words, by embedding them into a three-dimensional space).

(Analyzer)

The image processor 230 includes the analyzer 231. The analyzer 231 analyzes a front image acquired by photographing, by means of the infrared photographing optical system, the fundus Ef on which the split target (focusing index) is projected to obtain refractive power of the eye E. This front image is an observation image described above, for example.

Figure 4:
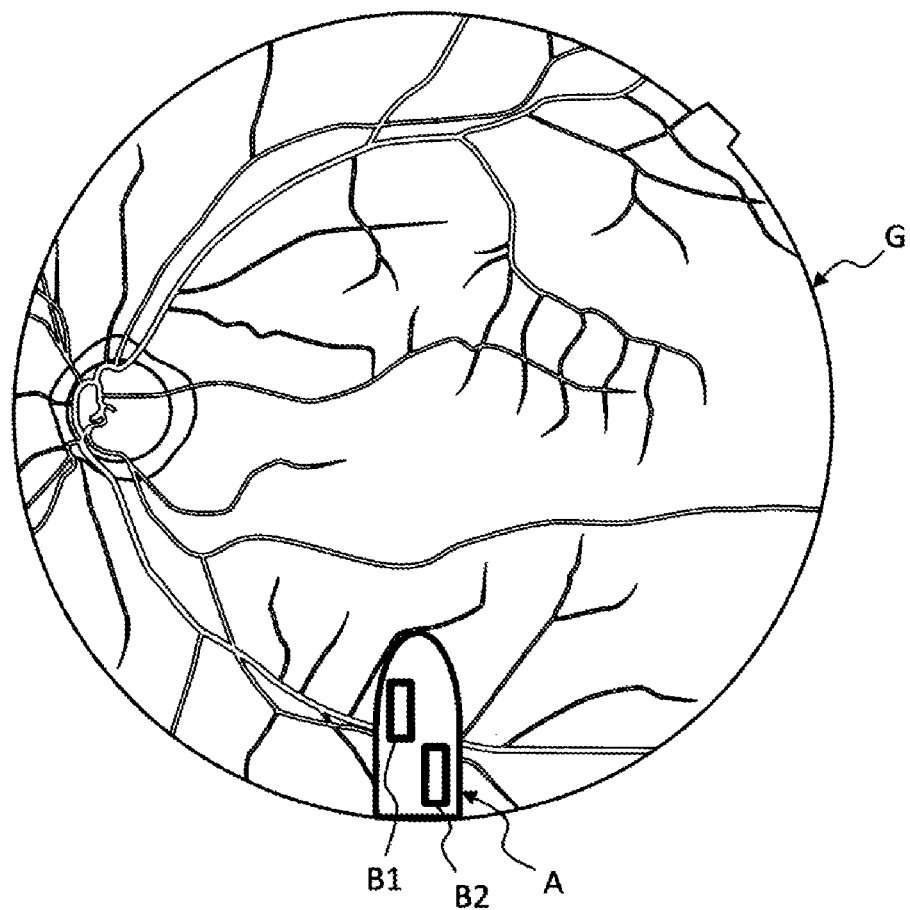
FIG. 4 is a schematic diagram for explaining a configuration example of an ophthalmologic observation apparatus according to an embodiment.

FIG. 4 illustrates an example of an observation image. The observation image G illustrated in FIG. 4 represents images of a pair of split targets (split-target images) B1 and B2 together with morphology of the fundus Ef. Symbol A indicates a shadow of the reflection rod 67 (reflection-rod image) disposed in the optical path of the illumination optical system 10. When focus of the imaging optical system 30 is adequate, that is, when the focusing lens 31 is located at an adequate position, the split-target images B1 and B2 are arranged in a line along the vertical direction in FIG. 4. On the other hand, when focus of the imaging optical system 30 is not adequate, the split-target images B1 and B2 are relatively shifted in the horizontal direction in FIG. 4. Direction and amount of the relative shift between the split-target images B1 and B2 correspond to direction and amount of deviation from a proper focusing state. Such focus deviation corresponds to the refractive power of the eye E.

The analyzer 231 stores information (target-image/refractive-power association information) in which directions and amounts of shift between the split-target images B1 and B2 and values of eye refractive power are associated with each other in advance. The analyzer 231 analyzes an observation image (or still image(s) included in the observation image) to obtain shift information (shift direction and shift amount) between the split-target images B1 and B2 represented in the observation image. Further, the analyzer 231 finds refractive power corresponding to the obtained shift information based on the target-image/refractive-power association information. This found value of refractive power is used as refractive power of the eye E.

Information of the refractive power of the eye E obtained by the analyzer 231 is sent to the target-position obtaining part 213. Based on this refractive power information and association information 212a, the target-position obtaining part 213 obtains target positions of the focusing lenses 31 and 43. This processing is executed in the same way as the above.

The image processor 230 that functions as above includes, for example, the aforementioned microprocessor, RAM, ROM, hard disk drive, circuit boards, etc. Computer programs causing the microprocessor to execute the above functions are stored in storage devices such as the hard disk drive in advance.

(User Interface)

A user interface 240 includes the display 240A and operation part 240B. The display 240A includes a display device in the arithmetic and control unit 200 and/or display device 3. The operation part 240B includes operation devices in the arithmetic and control unit 200. The operation part 240B may include various buttons, keys, etc. provided on cases of the ophthalmologic observation apparatus 1 or outside thereof. For example, when the retinal camera unit 2 has a case similar to conventional retinal cameras, a joy stick, operation panel, etc. provided on this case may be included in the operation part 240B. The display 240A may include various display devices such as a touch panel etc. provided on the case of the retinal camera unit 2.

The display 240A and operation part 240B are not necessarily separate components. For example, like a touch panel, a compound device of display and operation functions may be applied. In this case, the operation part 240B includes the touch panel and computer programs. Contents of operation to the operation part 240B are input into the controller 210 as electrical signals. Further, operations and/or information input may be performed by means of graphical user interface (GUI) displayed on the display 240A and operation part 240B.

[Signal Light Scanning and OCT Images]

Now, scanning of signal light LS and OCT images are explained.

Scanning modes of the signal light LS by the ophthalmologic observation apparatus 1 may include, for example, horizontal, vertical, crossed, radial, circular, concentric, helical scans, etc. Taking observation site of fundus, analysis mode (retinal thickness etc.), time required for scanning, density of scanning, etc. into account, these scanning modes are selectively used.

The horizontal scan is one for scanning signal light LS in the horizontal direction (x-direction). The horizontal scan includes a mode of scanning signal light LS along multiple scanning lines extending in the horizontal direction and arranged in the vertical direction (y-direction). In this mode, the interval between scanning lines may be set arbitrarily. By setting the interval between adjacent scanning lines to be sufficiently narrow, three-dimensional image may be formed (three-dimensional scan). The vertical scan is performed in a similar manner.

The crossed scan is one for scanning signal light LS along a cross-shape trajectory consisting of two linear trajectories (line trajectories) orthogonal to each other. The radial scan is one for scanning signal light LS along a radial trajectory consisting of multiple line trajectories arranged at predetermined angles. The crossed scan is an example of the radial scan.

The circular scan is one for scanning signal light LS along a circular trajectory. The concentric scan is one for scanning signal light LS along multiple circular trajectories arranged concentrically around a predetermined center position. The circular scan is an example of the concentric scan. The helical scan is one for scanning signal light LS along a helical trajectory while making the turning radius gradually smaller (or greater).

Since the galvano scanner 42 is configured to scan signal light LS in the directions orthogonal to each other, the galvano scanner 42 is capable of scanning signal light LS in the x and y-directions independently. Signal light LS may be scanned along an arbitrary trajectory on the xy-plane by simultaneously controlling the orientations of two galvano mirrors included in the galvano scanner 42. As a result, various scanning modes as described above may be realized.

By scanning signal light LS in the modes described as above, it is possible to obtain a cross-sectional image in a plane spanned by the direction along a scanning line and the fundus depth direction (z-direction). Moreover, when the interval between scanning lines is narrow, a three-dimensional image may be obtained.

A region in the fundus Ef to be scanned by signal light LS as described above, that is, a region in the fundus Ef subject to OCT is referred to as a scanning region. A scanning region of three-dimensional scan is a rectangular region in which multiple horizontal scans are arranged. A scanning region of concentric scan is a disciform region surrounded by the trajectory of the circular scan with maximum diameter. A scanning region of radial scan is a disciform (or polygonal) region connecting ends of scanning lines.

[Operations]

Figure 5:
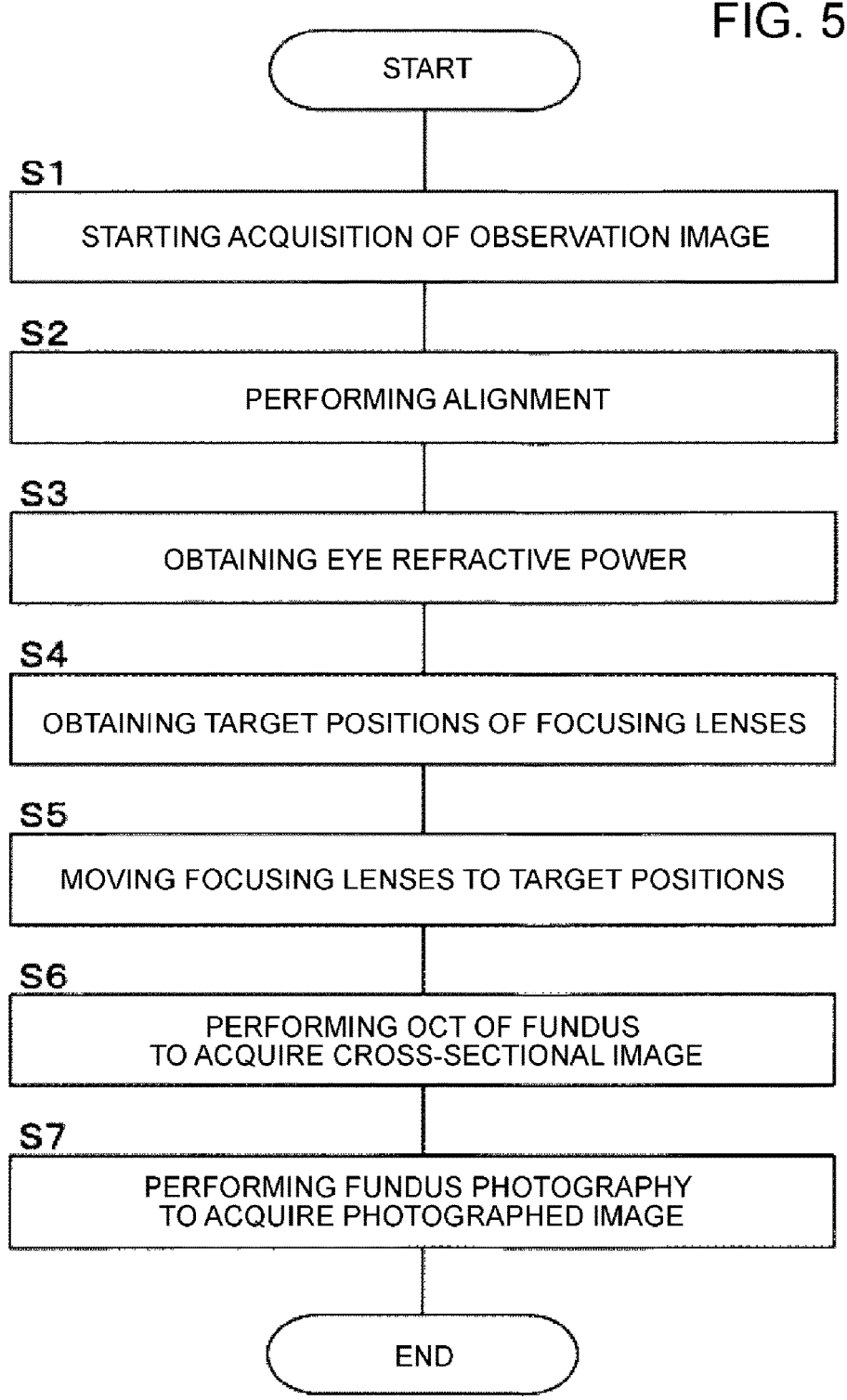
FIG. 5 is a flowchart representing an operation example of an ophthalmologic observation apparatus according to an embodiment.

Operations of the ophthalmologic observation apparatus 1 are described. FIG. 5 shows an example of an operation of the ophthalmologic observation apparatus 1.

(S1: Starting Acquisition of Observation Image)

Firstly, an observation image of the fundus Ef is acquired by continuously illuminating the fundus Ef with observation illumination light. The observation image is a near-infrared moving image acquired in real time until the continuous illumination is terminated. During this period of time, fixation target from the LCD 39 is projected on the eye E.

(S2: Performing Alignment)

Further, alignment target from the alignment optical system 50 and split target from the focus optical system 60 are projected on the eye E. Alignment-target images (illustration omitted) and split-target images B1 and B2 illustrated in FIG. 4 are represented in the observation image. The user or controller 210 performs alignment using the alignment targets (manual or automatic alignment).

(S3: Obtaining Eye Refractive Power)

The analyzer 231 analyzes (frame(s) of) the observation image) to obtain refractive power of the eye E. More specifically, the analyzer 231 obtain refractive power of the eye E based on the positions of the split-target images B1 and B2 represented in the observation image.

(S4: Obtaining Target Positions of Focusing Lenses)

Based on the refractive power of the eye E obtained in Step 3 and the association information 212a stored in the storage 212 in advance, the target-position obtaining part 213 obtains a target position (first target position) of the focusing lens 31 in the imaging optical system 30 and a target position (second target position) of the focusing lens 43 in the optical system for OCT (measuring optical system).

(S5: Moving Focusing Lenses to Target Positions)

The main controller 211 controls the focus driver 31A so as to move the focusing lens 31 to the first target position obtained in Step 4. Further, the main controller 211 controls the focus driver 43A so as to move the focusing lens 43 to the second target position obtained in Step 4. The main controller 211 may execute these controls in parallel or may execute one control after the other. Further, the main controller 211 is capable of recognizing current positions of the focusing lenses 31 and 43. For example, a position sensor(s) that detects positions of the respective focusing lenses 31 and 43 may be provided. Alternatively, a configuration is applicable in which history of controls of the respective focusing lenses 31 and 43 (for example, contents of pulse signals transmitted to the respective focus drivers 31A and 43A during the period from a timing at which the focusing lenses 31 and 43 are located at preset initial positions up to now) is recorded. The main controller 211 sends control signals for moving the focusing lens 31 from the current position to the first target position to the focus driver 31A, and sends control signals for moving the focusing lens 43 from the current position to the second target position to the focus driver 43A. As a result, the focusing lens 31 is located at the first target position and the focusing lens 43 is located at the second target position.

(S6: Performing OCT of Fundus to Acquire Cross-Sectional Image)

The main controller 211 controls the OCT unit 100, optical-path-length changing part 41, galvano scanner 42, etc. to perform OCT of the fundus Ef. Data acquired by OCT is sent to the image forming part 220 as detection signals from the CCD 115. The image forming part 220 forms a cross-sectional image of the fundus Ef based on the detection signals. The main controller 211 displays the formed cross-sectional image on the display 240A. Further, the main controller 211 stores the formed cross-sectional image in the storage 212.

(S7: Performing Fundus Photography to Acquire Photographed Image)

The main controller 211 controls the illumination optical system 10 (imaging light source 15 etc.) and imaging optical system 30 to acquire a photographed image of the fundus Ef. The main controller 211 displays the acquired photographed image on the display 240A. Further, the main controller 211 stores the acquired photographed image in the storage 212. This completes the present operation example.

[Actions and Effects]

Actions and effects of the ophthalmologic observation apparatus 1 are explained.

The ophthalmologic observation apparatus 1 of the present embodiment includes a photographing optical system, measuring optical system, optical-path coupler, first and second drivers and controller. The photographing optical system performs photography for acquiring a front image of the eye E and includes a first focusing lens. In the present embodiment, the photographing optical system includes the illumination optical system 10 and imaging optical system 30, and the focusing lens 31 corresponds to the first focusing lens. The measuring optical system performs OCT for acquiring a cross-sectional image of the eye E and includes a second focusing lens. In the present embodiment, the measuring optical system includes the optical system housed in the OCT unit 100 and optical system forming an optical path from the collimator lens unit 40 to the objective lens 22, and the focusing lens 43 corresponds to the second focusing lens. The optical-path coupler couples an optical path of the photographing optical system and optical path of the measuring optical system at a location on the eye side than the first and second focusing lenses. The "location on the eye side than the focusing lenses" indicates a location, in optical paths of the respective optical systems, on the eye side than focusing lenses. In the present embodiment, the dichroic mirror 46 corresponds to the optical-path coupler. As can be seen from the configuration of the optical-path coupler, the first and second focusing lenses are separate optical elements. The first driver moves the first focusing lens along an optical axis of the photographing optical system. In the present embodiment, the focus driver 31A corresponds to the first driver. The second driver moves the second focusing lens along an optical axis of the measuring optical system. In the present embodiment, the focus driver 43A corresponds to the second driver. The controller controls the first and second drivers individually. In the present embodiment, the controller 210 corresponds to the controller.

According to the ophthalmologic observation apparatus 1, the photographing optical system and measuring optical system have the respective individual focusing lenses, and these focusing lenses may be controlled individually. Therefore, the first focusing lens may be positioned at an optimal focus position for acquiring front images and the second focusing lens may be positioned at an optimal focus position for OCT. Consequently, it is possible to perform both front-image acquisition and OCT of the eye E with suitable focus conditions.

In the present embodiment, the photographing optical system performs photography for acquiring front images of the fundus Ef and the measuring optical system performs OCT for acquiring cross-sectional images of the fundus Ef. Further, the ophthalmologic observation apparatus 1 of the present embodiment includes a refractive-power obtaining part that obtains refractive power of the eye E. Moreover, the controller 210 includes a first target-position obtaining part (target-position obtaining part 213) that obtains target positions of the first and second focusing lenses based on the refractive power obtained by the target-position obtaining part. Then, the controller 210 controls the first driver so as to move the first focusing lens to the first target position obtained by the first target-position obtaining part and controls the second driver so as to move the second focusing lens to the second target position. Although the present embodiment performs both movement controls of the first and second focusing lenses, it is possible to perform any one of the movement controls. If this is the case, the other of the movement controls may be performed in an arbitrary way.

According to such an embodiment, both front-image acquisition and OCT of the fundus Ef may be performed with suitable focus conditions. Further, movement controls of the focusing lens(es) may be performed automatically. In addition, because such movement controls may be performed in accordance with refractive power of the eye E, focus adjustment may be performed with high accuracy.

Processing of obtaining refractive power of the eye E may be performed in the following way, for example. As a prerequisite, the photographing optical system includes an infrared photographing optical system that uses infrared light to perform photography of the fundus. In the present embodiment, the infrared photographing optical system includes the optical system that irradiates observation illumination light from the observation light source 11 on the fundus Ef and optical system that detects fundus reflected light of the observation illumination light by means of the CCD 35. The refractive-power obtaining part includes the projecting optical system and analyzer. The projecting optical system projects, onto the fundus Ef, the focusing index indicating a state of focus of the photographing optical system on the fundus Ef. In the present embodiment, the projecting optical system includes the focus optical system 60, and the split target corresponds to the focusing index. The analyzer 231 analyzes a front image acquired by photographing, using the infrared photographing optical system, the fundus Ef on which the focusing index is projected to obtain the refractive power of the eye E.

According to such an embodiment, because refractive power may be obtained by actually measuring the eye E, it is possible to perform focus adjustment with high accuracy.

Processing of obtaining a target position(s) of the focusing lens(es) may be performed in the following way, for example. To begin with, the controller 210 stores association information 212a in which values of eye refractive power and positions of the focusing lenses are associated with each other in advance. The association information 212a includes first association information in which values of eye refractive power and positions of the first focusing lens are associated with each other, and second association information in which values of eye refractive power and positions of the second focusing lens are associated with each other. The first target-position obtaining part (target-position obtaining part 213) obtains the target positions of the first and second focusing lenses based on the refractive power obtained by the refractive-power obtaining part and the first and second association information. More specifically, the first target-position obtaining part obtains a target position of the first focusing lens based on the refractive power obtained by the refractive-power obtaining part and the first association information, and obtains a target position of the second focusing lens based on the refractive power and the second association information.

According to such an embodiment, focus adjustments of both optical systems may be performed by obtaining target positions of both focusing lenses 31 and 43 on the basis of refractive power of the eye E and the association information 212*a*. Consequently, it is possible to perform both front-image acquisition and OCT of the eye E with suitable focus conditions.

Second Embodiment

The present embodiment explains an ophthalmologic observation apparatus configured to perform focusing for front-image acquisition by using result of focusing for OCT. In fundus examination, for example, taking myosis of an eye into consideration, visible-light photography is usually performed after OCT. The present embodiment is effective for examinations in such order.

[Configurations]

An ophthalmologic observation apparatus of the present embodiment has overall configuration and optical systems similar to the first embodiment. Control system is also almost the same as the first embodiment. In the following explanation, same symbols are used for components similar to those in the first embodiment.

Figure 6:
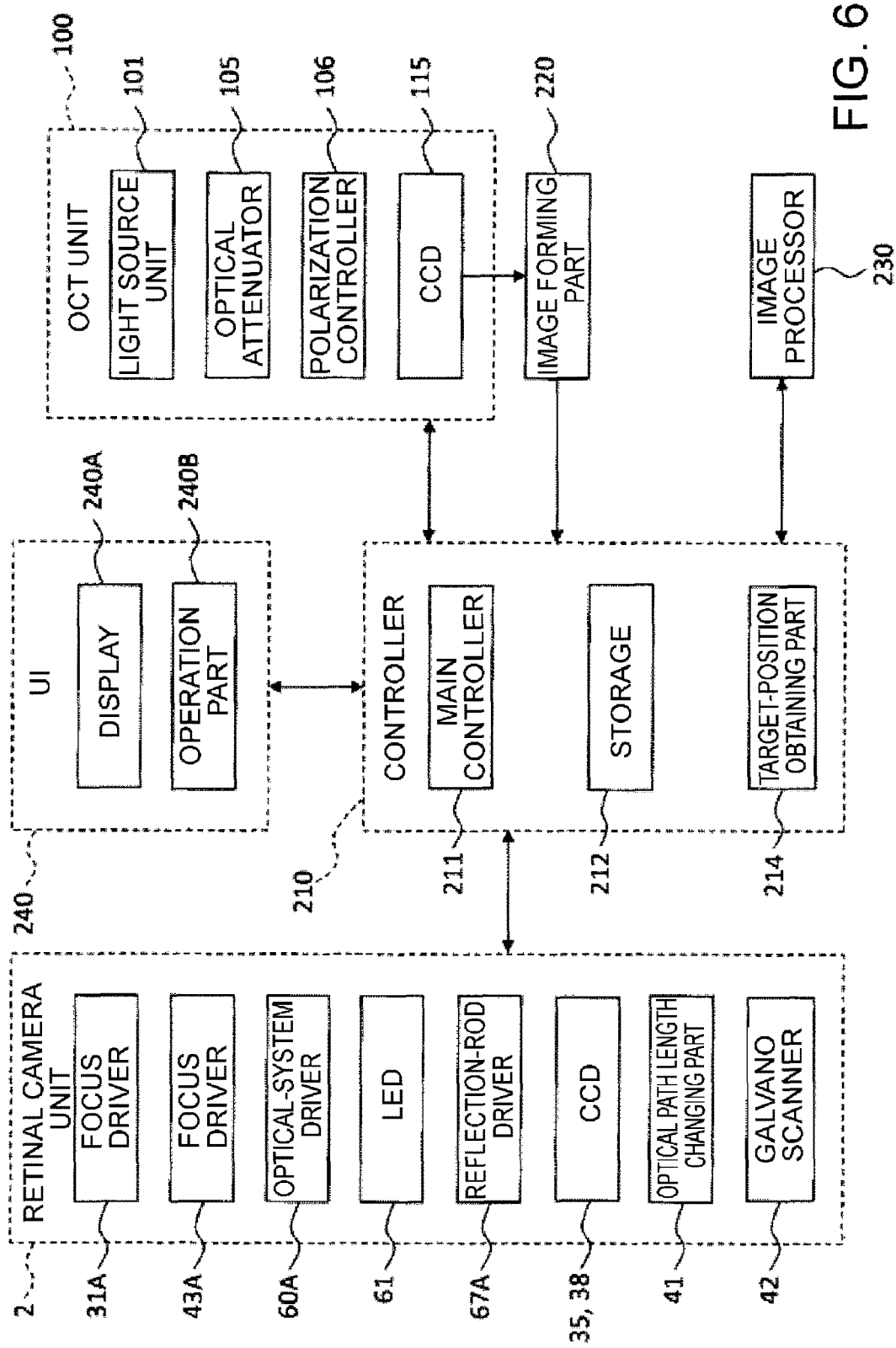
FIG. 6 is a schematic block diagram illustrating a configuration example of an ophthalmologic observation apparatus according to an embodiment.

FIG. 6 illustrates a configuration example of a control system of the ophthalmologic observation apparatus of the present embodiment. In the present embodiment, a target-position obtaining part 214 is provided instead of the target-position obtaining part 213 of the first embodiment. Further, the association information 212*a* is not necessarily stored in the storage 212, and/or the analyzer 231 is not necessarily provided in the image processor 230. Hereinafter, such differences are especially described.

Based on the position of the focusing lens 43 in the measuring optical system during OCT, the target-position obtaining part 214 obtains a target position of the focusing lens 31 in the imaging optical system 30. The target-position obtaining part 214 is an example of a second target-position obtaining part.

An example of processing executed by the target-position obtaining part 214 is explained. Before performing OCT, focus adjustment for OCT is carried out. This focus adjustment may be performed using an infrared fundus image (observation image) and split target as in the first embodiment; however, fine adjustment using OCT images may be additionally performed. For example, repeatedly performing OCT to substantially the same cross section of the fundus Ef, a moving image of this cross section (OCT moving image) may be acquired. Frame rate of the OCT moving image corresponds to frequency of repetition of OCT.

By displaying the OCT moving image on the display 240A, the user may focus adjustment manually.

Technology is known in which focus adjustment is automatically performed by analyzing the OCT moving image (or still image(s) included therein) using the ophthalmologic observation apparatus. An example of this analysis includes: analyzing pixel values (brightness values) of a still image(s) included in the OCT moving image to specify a region(s) with high image quality (high-image-quality region(s)); and specifying current focus position based on the position (z-coordinate) of the high-image-quality region in the depth direction (z-direction) of the frame. Further, if a tissue(s) (retinal surface, retinal pigment epithelium, choroid, etc.) of the fundus Ef to be focused on is previously determined, the image processor 230 specifies a region corresponding to the concerned tissue (target region) in the still image. Alternatively, the user may designate a target region. The image processor 230 finds a position (z-coordinate) of the target region in the depth direction (z-direction) of the frame. The main controller 211 generates a control signal for changing the current focus position of the measuring optical system to a focus position corresponding to the target region, and transmits the control signal to the focus driver 43. Accordingly, the focusing lens 43 is arranged at the position corresponding to the target region.

Here positions in the depth direction (z-direction) of frames and positions of focusing lens 43 in the measuring optical system may be associated with each other in advance based on configuration of the measuring optical system. It is also possible to provide a function for correcting this association by taking refractive power of the eye E etc. into account.

The fundus Ef represented as an OCT moving image moves in the frames due to eye movement and pulsebeat moves; however, there is technology for fixing the image of the fundus Ef at a predetermined location in the frames by controlling the optical-path-length changing part 41 so as to follow the movement of this image. Methods of focus adjustment using OCT images are not limited to the above examples and any method may be applied.

Based on the position of the focusing lens 43 set by focus adjustment using OCT images as the above, the target-position obtaining part 214 acquires a target position of the focusing lens 31 in the imaging optical system 30.

Examples of this processing are described. Information associating positions of the focusing lenses 31 with positions of the focusing lenses 43 may be stored in the storage 212 in advance, and a position of the focusing lens 31 corresponding to the position of the focusing lens 43 applied during OCT may be obtained by referring to the stored information. Here, this information may be created through the medium of the value of eye refractive power as described in the first embodiment, for example. Alternatively, this information may be created by referring to configurations of the photographing optical system and measuring optical system, difference between wavelengths of light used for fundus photography and wavelengths of light used for OCT. If refractive power of the eye E is known, this information may be created or corrected based on the value of this refractive power. The above examples are not intended to limit processing of obtaining a position of the focusing lens 31 from the position of the focusing lens 43 during OCT, and the target-position obtaining part 214 may perform this processing in an arbitrary way.

The main controller 211 controls the focus driver 31 so as to move the focusing lens 31 to the target position obtained by the target-position obtaining part 214.

[Operations]

Figure 7:
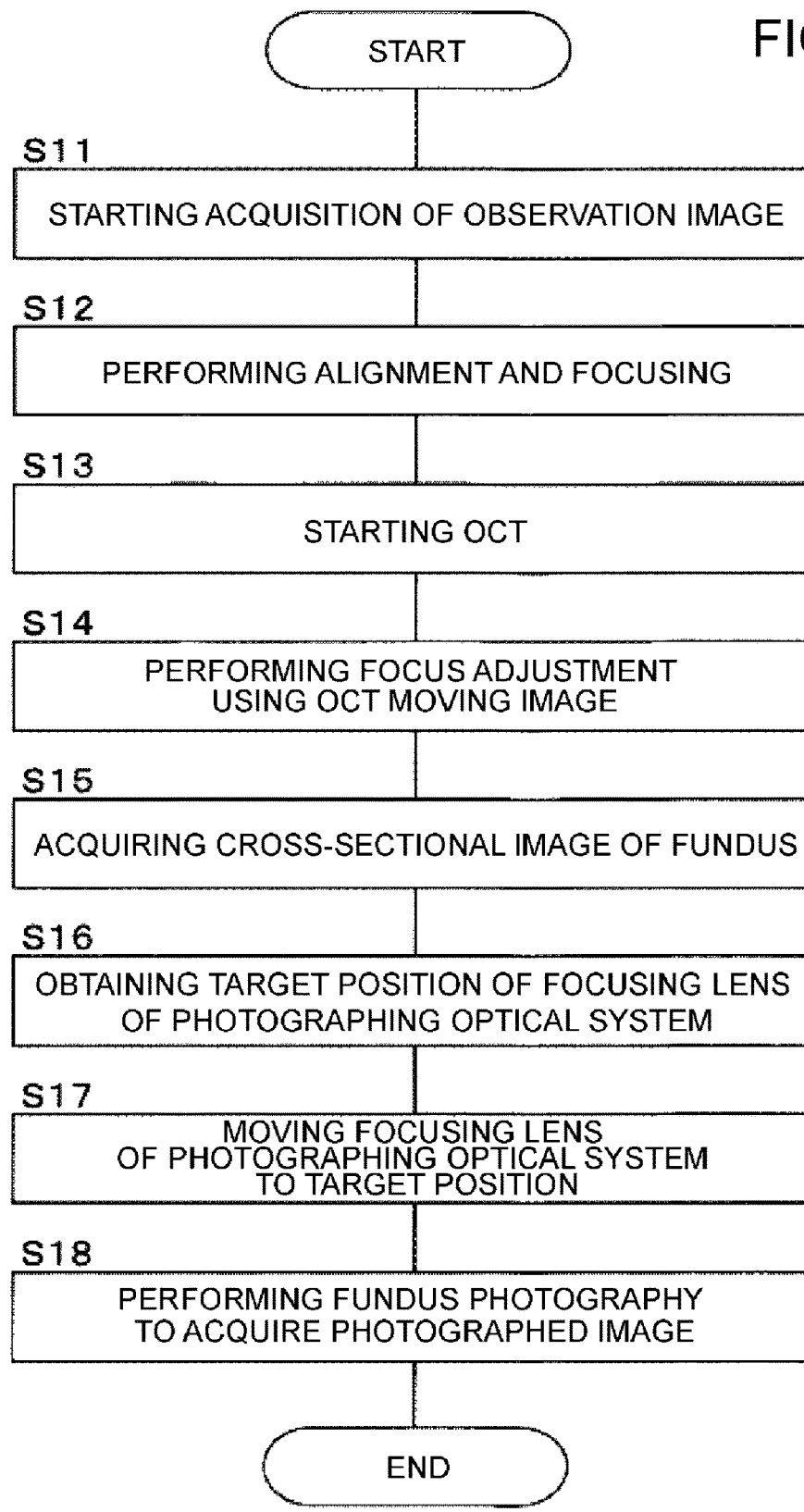
FIG. 7 is a flowchart representing an operation example of an ophthalmologic observation apparatus according to an embodiment.

Operations of the ophthalmologic observation apparatus of the present embodiment are described. FIG. 7 shows an example of an operation of the ophthalmologic observation apparatus.

(S11: Starting Acquisition of Observation Image)

As with the first embodiment, acquisition of observation image is commenced and fixation of the eye E is performed.

(S12: Performing Alignment and Focusing)

Alignment target and split target are projected on the eye E as with the first embodiment. Then, alignment using the alignment target and focus adjustment using the split target are carried out. This focus adjustment is performed for both of the photographing optical system and measuring optical system.

(S13: Starting OCT)

The main controller 211 controls the OCT unit 100, optical-path-length changing part 41, galvano scanner 42, etc. to start OCT of the fundus Ef. This OCT is repeatedly performed to substantially the same cross section of the fundus Ef. In other words, this OCT is performed in an operation mode for acquiring OCT moving images.

(S14: Performing Focus Adjustment using OCT Moving Image)

The user or ophthalmologic observation apparatus performs fine focus adjustment using an OCT moving image.

(S15: Acquiring Cross-Sectional Image of Fundus)

When the fine focus adjustment in Step 14 is completed or when the user performs a predetermined operation, the main controller 211 controls the OCT unit 100, optical-path-length changing part 41, galvano scanner 42, etc. to perform OCT of the fundus Ef. This OCT is carried out in a preset mode. Accordingly, a cross-sectional image(s) to be used for diagnosis is acquired.

(S16: Obtaining Target Position of Focusing Lens of Photographing Optical System)

When OCT is completed or when the user performs a predetermined operation, the target-position obtaining part 214 obtains a target position of the focusing lens 31 in the photographing optical system based on the position of the focusing lens 43 applied to OCT in Step 15, that is, based on the position of the focusing lens 43 achieved by the focus adjustment in Step 14.

(S17: Moving Focusing Lens of Photographing Optical System to Target Position)

The main controller 211 controls the focus driver 31A so as to move the focusing lens 31 to the target position obtained in Step 16.

(S18: Performing Fundus Photography to Acquire Photographed Image)

The main controller 211 controls the illumination optical system 10 (imaging light source 15 etc.) and imaging optical system 30 to acquire a photographed image of the fundus Ef. The main controller 211 displays the acquired photographed image on the display 240A. Further, the main controller 211 stores the acquired photographed image in the storage 212. This completes the present operation example.

[Actions and Effects]

Actions and effects of the ophthalmologic observation apparatus of the present embodiment are explained.

The ophthalmologic observation apparatus of the present embodiment includes a photographing optical system, measuring optical system, optical-path coupler, first and second drivers and controller. Consequently, the photographing optical system and measuring optical system have the respective individual focusing lenses, and these focusing lenses may be controlled individually. Therefore, the first focusing lens may be positioned at an optimal focus position for acquiring front images and the second focusing lens may be positioned at an optimal focus position for OCT. Therefore, it is possible to perform both front-image acquisition and OCT of the eye E with suitable focus conditions.

In the present embodiment, the controller (210) includes the target-position obtaining part 214 (second target-position obtaining part) that obtains a target position of the focusing lens 31 in the photographing optical system based on the position of the focusing lens 41 of the measuring optical system during OCT further, the controller controls the focus driver 31A so as to move the focusing lens 31 to the target position obtained by the target-position obtaining part 214.

The embodiment thus configured is capable of acquiring front images of the eye E with a good focus condition because focus adjustment of the photographing optical system may be performed by referring to the result of focus adjustment using OCT images with high precision and high accuracy. Further, there is a risk that the photographing optical system becomes out of focus during OCT due to eye movement etc. Regarding such situations, the present embodiment is capable of performing photography for front-image acquisition with suitable focus conditions because focus adjustment of the photographing optical system may be performed from the focus condition during OCT. Further, the present embodiment does not bother the user because focus adjustment of the photographing optical system may be executed automatically after OCT.

Processing of obtaining target position of the focusing lens 31 in the photographing optical system may be performed based on OCT moving images. More specifically, in the present embodiment, the measuring optical system repeatedly performs OCT to substantially the same cross section of the eye, thereby acquiring an OCT moving image of this cross section. Further, the target-position obtaining part 214 may obtain a target position of the focusing lens 31 in the photographing optical system from the position of the focusing lens 43 that has been set based on a plurality of cross-sectional images (that is, frames of the OCT moving image) acquired by the repetitive OCT.

When an OCT moving image is used like this, the image corresponding to the fundus Ef may be fixed at a predetermined position in the frames as described above. Therefore, a target position of the focusing lens 31 in the photographing optical system may be obtained with high accuracy even when eye movement, pulsebeat, etc. occur during OCT Third Embodiment The present embodiment explains user interfaces for performing focus adjustment of the photographing optical system and measuring optical system based on OCT images.

[Configurations]

An ophthalmologic observation apparatus of the present embodiment has overall configuration and optical systems similar to the first embodiment. Control system is also almost the same as the first embodiment. In the following explanation, same symbols are used for components similar to those in the first embodiment.

Figure 8:
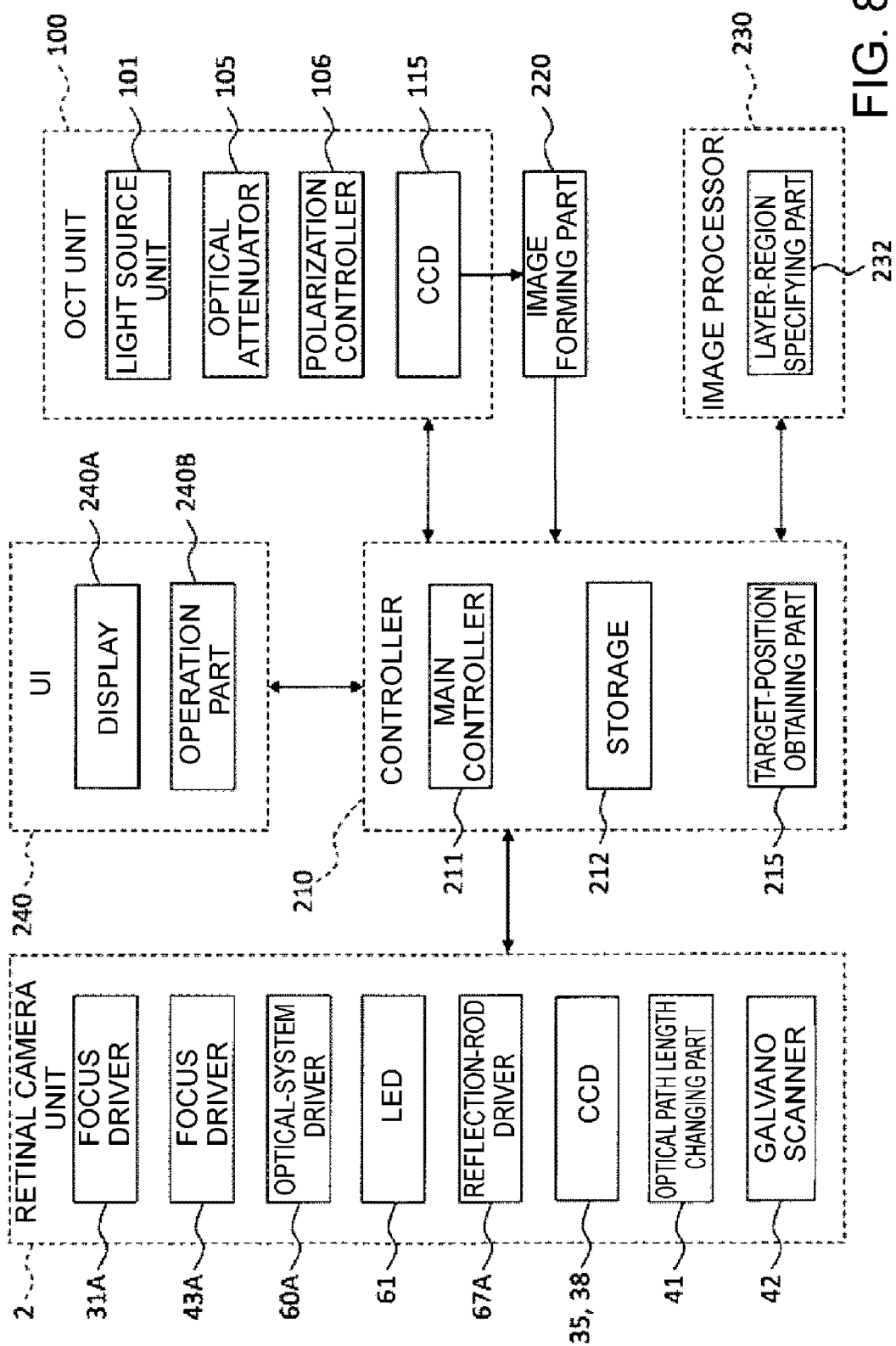
FIG. 8 is a schematic block diagram illustrating a configuration example of an ophthalmologic observation apparatus according to an embodiment.

FIG. 8 illustrates a configuration example of a control system of the ophthalmologic observation apparatus of the present embodiment. In the present embodiment, a target-position obtaining part 215 is provided instead of the target-position obtaining part 213 of the first embodiment. Further, the association information 212a is not necessarily stored in the storage 212, and/or the analyzer 231 is not necessarily provided in the image processor 230. Further, the image processor 230 includes a layer-region specifying part 232. Hereinafter, such differences are especially described.

The main controller 211 displays cross-sectional images of the fundus Ef acquired by OCT on the display 240A. The user uses the operation part 240B to designate a desired position in the cross-sectional image displayed on the display 240A. The desired position is a position (focus-target position) in the cross-section on which the user wants to focus.

The focus-target position may be a focus-target position for the measuring optical system and/or a focus-target position for the photographing optical system. A user interface capable of designating both focus-target positions may be provided, or a user interface capable of designating only one of these may be provided.

The focus-target positions of both the optical systems may be the same or different. In the former case, a user interface capable of designating both focus-target positions individually or at once is provided. In the latter case, a user interface capable of designating both focus-target positions individually is provided. In the case in which relationship between both focus-target positions is determined in advance based on eye refractive power, wavelength, etc., a configuration may be employed in which one of the focus-target positions is automatically designated based on the result of designation of the other. Concrete configurations of the user interfaces exemplified herein are arbitrary.

The target-position obtaining part 215 obtains a target position of the focusing lens 31 (first target position) and/or a target position of the focusing lens 43 (second target position) based on a position designated in a cross-sectional image using the operation part 240B. The target-position obtaining part 215 is an example of a third target-position obtaining part. The target-position obtaining part 215 executes arbitrary processing for acquiring these target positions. Hereinafter, examples of configurations of user interfaces and processing executed by the target-position obtaining part 215 are explained.

First Processing Example

Figure 9:
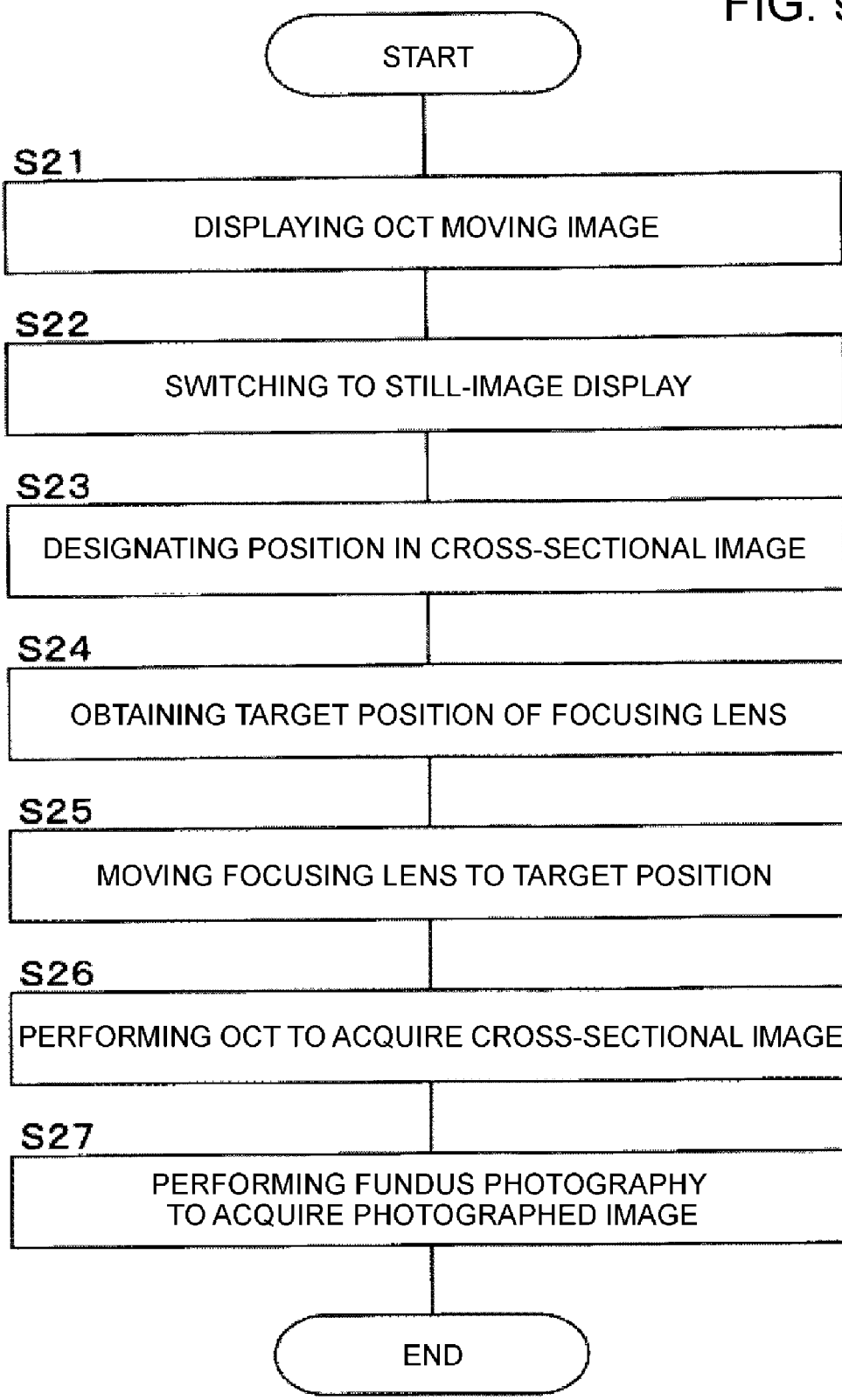
FIG. 9 is a flowchart representing an operation example of an ophthalmologic observation apparatus according to an embodiment.

A first processing example is described with referring to FIG. 9. In this processing example, an OCT moving image is frozen (that is, switched to still-image display) and a focus position is designated.

(S21: Displaying OCT Moving Image)

The main controller 211 controls the OCT unit 100, optical-path-length changing part 41, galvano scanner 42, etc. to perform repetitive OCT to substantially the same cross section of the eye E (fundus Ef). Based on a plurality of cross-sectional images acquired by this repetitive OCT, the main controller 211 displays an OCT moving image on the display 240A in real time.

(S22: Switching to Still-Image Display)

In response to performance of a predetermined operation (operation for designating still-image display) using the operation part 240B, the main controller 211 switches modes of displaying cross-sectional images from moving-image display to still-image display.

Here, a still image and moving image may be displayed side by side. For example, a display region for displaying a still image (still-image display region) is provided in a display screen in addition to a display region of a real-time OCT moving image. Further, in response to designation of still-image display, leaving display of the OCT moving image, it is possible to display, on the still-image display region, a frame (still image) of the OCT moving image corresponding to the timing at which the designation is performed. When the designation is performed multiple times, still images displayed on the still-image display region may be updated each time the designation is performed. Alternatively, it is possible to display still images obtained each time the designation is performed side by side.

Here, a plurality of still images may be displayed in the same size, part of the still images may be reduced in size (displayed as thumbnails, etc.), or display of part of the still images may be finished.

(S23: Designating Position in Cross-Sectional Image)

The user operates the operation part 240B to designate a desired position in the cross-sectional image displayed as a still image. The designated position is a position indicating a desired tissue of the fundus Ef represented in the cross-sectional image, for example.

The number of designated positions is arbitrary. For example, it is possible to individually designate positions indicating sites (retinal surface etc.) to be observed in detail with a photographed image and positions indicating sites (retinal pigment epithelium, choroid, etc.) to be observed in detail with a cross-sectional image. When two or more positions are designated, information that makes respective designated positions discriminative may be input. For example, information indicating that a first designated position is a position for fundus photography and information indicating that a second designated position is a position for OCT may be input.

When a single position is designated, the designated position is treated as one for a predetermined purpose (for OCT or fundus photography).

Information indicating a designated position(s) may be displayed together with a cross-sectional image(s). For example, an image indicating a designated position may be displayed over a cross-sectional image. When the apparatus possesses the aforementioned function that OCT moving image follows eye movement, pulsebeat, etc., it is also possible to change information indicating the designated position chronologically so as to follow eye movement etc. An image indicating the designated position may also be changed chronologically in response to switch of display mode of cross-sectional image to movie display.

(S24: Obtaining Target Position of Focusing Lens)

Based on the position in the cross-sectional image designated in Step 23, the target-position obtaining part 215 obtains a target position of the focusing lens 31 (first target position) and/or target position of the focusing lens 43 (second target position).

Processing of obtaining the first target position is executed based on a coordinate (z-coordinate) of the first target position in the depth direction (z-direction) in the frame of the cross-sectional image, for example. Processing of obtaining the second target position is executed based on a coordinate (z-coordinate) of the second target position in the depth direction (z-direction) in the frame of the cross-sectional image, for example. Here, it is assumed that z-coordinates in the frames and positions of focusing lens 31 and/or focusing lens 43 are associated with each other in advance. Target position(s) may be corrected based on eye refractive power etc.

(S25: Moving Focusing Lens to Target Position)

When the first target position is obtained in Step 24, the main controller 211 controls the focus driver 31A to move the focusing lens 31 to the first target position. When the second target position is obtained in Step 24, the main controller 211 controls the focus driver 43A to move the focusing lens 43 to the second target position.

(S26: Performing OCT to Acquire Cross-Sectional Image)

The main controller 211 controls the OCT unit 100, optical-path-length changing part 41, galvano scanner 42, etc. to perform OCT of the fundus Ef. The image forming part 220 forms a cross-sectional image of the fundus Ef based on detection signals from the CCD 115. The main controller 211 displays the formed cross-sectional image on the display 240A. Further, the main controller 211 stores the formed cross-sectional image in the storage 212.

(S27: Performing Fundus Photography to Acquire Photographed Image)

The main controller 211 controls the illumination optical system 10 (imaging light source 15 etc.) and imaging optical system 30 to acquire a photographed image of the fundus Ef. The main controller 211 displays the acquired photographed image on the display 240A. Further, the main controller 211 stores the acquired photographed image in the storage 212. This completes the present operation example.

Second Processing Example

Figure 10:
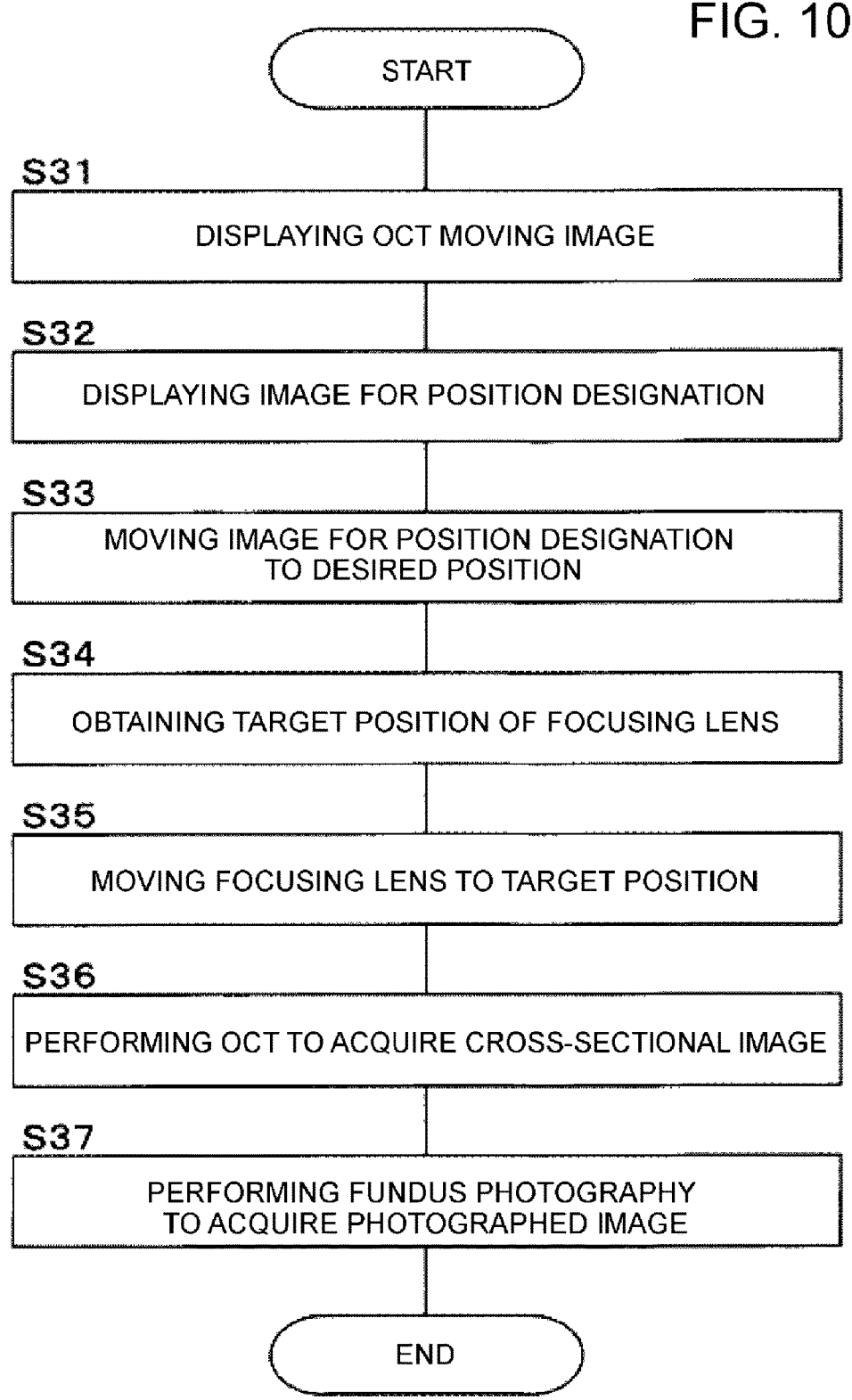
FIG. 10 is a flowchart representing an operation example of an ophthalmologic observation apparatus according to an embodiment.

A second processing example is described with referring to FIG. 10. In this processing example, a focus position is designated by moving an image for position designation, displayed on an OCT moving image, to a desired position.

(S31: Displaying OCT Moving Image)

The main controller 211 controls the OCT unit 100, optical-path-length changing part 41, galvano scanner 42, etc. to perform repetitive OCT to substantially the same cross section of the eye E (fundus Ef). Based on a plurality of cross-sectional images acquired by this repetitive OCT, the main controller 211 displays an OCT moving image on the display 240A in real time.

(S32: Displaying Image for Position Designation)

The main controller 211 displays an image for position designation at a location in the OCT moving image corresponding to the focus position (that is, position of the focusing lens 43) during the repetitive OCT in Step 31.

When z-coordinates in (frame of) OCT moving image and positions of the focusing lens 43 are associated in advance, the main controller 211 obtains a position (z-coordinate) in OCT moving image corresponding to the position of the focusing lens 43 during OCT, and displays the image for position designation over the obtained position. Display position of the image for position designation may be corrected based on refractive power of the eye E etc.

The image for position designation may be a linear image passing the above position (z-coordinate) and orthogonal to the depth direction (z-direction). The image for position designation may be a linear or arrow-shaped image displayed at a location outside OCT moving image corresponding to the above position (z-coordinate). In general, the image for position designation is an image displayed over or near OCT moving image and has a function of indicating focus position in the OCT moving image.

When the apparatus possesses the aforementioned function that OCT moving image follows eye movement, pulsebeat, etc., it is possible to change display position of the image for position designation chronologically so as to follow eye movement etc.

The number of images for position designation displayed is arbitrary. For example, it is possible to individually display a first image for position designation for designating sites (retinal surface etc.) to be observed in detail with a photographed image and second image for position designation for designating sites (retinal pigment epithelium, choroid, etc.) to be observed in detail with a cross-sectional image. When two or more images for position designation are displayed, respective images for position designation may be displayed in a discriminative way. For example, display aspects (display colors etc.) of first and second images for position designation may be different.

When a single image for position designation is displayed, the image for position designation is used for a predetermined purpose (for OCT or fundus photography).

(S33: Moving Image for Position Designation to Desired Position)

The user operates the operation part 240B to move the image for position designation to a desired position. The desired position indicates a desired tissue of the fundus Ef represented in the cross-sectional image, for example.

(S34: Obtaining Target Position of Focusing Lens)

Based on the position of the image for position designation after movement in Step 33, the target-position obtaining part 215 obtains a target position of the focusing lens 31 (first target position) and/or target position of the focusing lens 43 (second target position).

Processing of obtaining the first target position is executed based on a coordinate (z-coordinate) of the image for position designation in the depth direction (z-direction) in the frame of the cross-sectional image, for example. Processing of obtaining the second target position is executed based on a coordinate (z-coordinate) of the image for position designation in the depth direction (z-direction) in the frame of the cross-sectional image, for example. Here, it is assumed that z-coordinates in the frames and positions of focusing lens 31 and/or focusing lens 43 are associated in advance. Target position(s) may be corrected based on eye refractive power etc.

(S35: Moving Focusing Lens to Target Position)

When the first target position is obtained in Step 34, the main controller 211 controls the focus driver 31A to move the focusing lens 31 to the first target position. When the second target position is obtained in Step 34, the main controller 211 controls the focus driver 43A to move the focusing lens 43 to the second target position.

(S36: Performing OCT to Acquire Cross-Sectional Image)

The main controller 211 controls the OCT unit 100, optical-path-length changing part 41, galvano scanner 42, etc. to perform OCT of the fundus Ef. The image forming part 220 forms a cross-sectional image of the fundus Ef based on detection signals from the CCD 115. The main controller 211 displays the formed cross-sectional image on the display 240A. Further, the main controller 211 stores the formed cross-sectional image in the storage 212.

(S37: Performing Fundus Photography to Acquire Photographed Image)

The main controller 211 controls the illumination optical system 10 (imaging light source 15 etc.) and imaging optical system 30 to acquire a photographed image of the fundus Ef. The main controller 211 displays the acquired photographed image on the display 240A. Further, the main controller 211 stores the acquired photographed image in the storage 212. This completes the present operation example.

Other Processing Examples

In the first and second processing examples described above, the following processing may be performed. The layer-region specifying part 232 analyzes a cross-sectional image (still image included in an OCT moving image) displayed on the display 240A to specify a layer region in this cross-sectional image corresponding to a predetermined layer. The layer region is an image region corresponding to at least one of layer tissues of the fundus Ef that has a layer structure. Specifically, the layer tissues of the fundus Ef include inner limiting membrane, nerve fiber layer, ganglion cell layer, inner plexiform layer, inner nuclear layer, outer plexiform layer, outer nuclear layer, outer limiting membrane, stratum neuroepitheliale, retinal pigment epithelium, choroid, sclera, etc.

The main controller 211 displays an image (layer image) indicating the layer region specified by the layer-region specifying part 232 over the cross-sectional image. When the apparatus possesses the aforementioned function that OCT moving image follows eye movement, pulsebeat, etc., the main controller 211 may change display position of the image for position designation chronologically so as to follow eye movement etc.

[Actions and Effects]

Actions and effects of the ophthalmologic observation apparatus of the present embodiment are explained.

The ophthalmologic observation apparatus of the present embodiment includes a photographing optical system, measuring optical system, optical-path coupler, first and second drivers and controller. Consequently, the photographing optical system and measuring optical system have the respective individual focusing lenses, and these focusing lenses may be controlled individually. Therefore, the first focusing lens may be positioned at an optimal focus position for acquiring front images and the second focusing lens may be positioned at an optimal focus position for OCT. Therefore, it is possible to perform both front-image acquisition and OCT of the eye E with suitable focus conditions.

The ophthalmologic observation apparatus of the present embodiment includes the display (240A) and operation part (240B). The display displays a cross-sectional image acquired by OCT. The operation part is used for designating a position in the cross-sectional image displayed by the display. Further, the controller (210) of the present embodiment includes a third target-position obtaining part (target-position obtaining part 215). The third target-position obtaining part obtains a target position of the first focusing lens (focusing lens 31) and/or a target position of the second focusing lens (focusing lens 43) based on the position designated by means of the operation part. Then, the controller controls the first driver (focus driver 31A) and/or the second driver (focus driver 43A) so as to move the first focusing lens and/or second focusing lens to the target position obtained by the third target-position obtaining part.

In the case in which the measuring optical system repeatedly performs OCT to substantially the same cross section of the eye, the display may display a plurality of cross-sectional images acquired by the repetitive OCT as a movie. Further, the controller switches the movie display to still-image display in response to a predetermined operation performed using the operation part. Then, based on a position designated, using the operation part, to a cross-sectional image displayed as a still image, the third target-position obtaining part may obtain the target position(s) of the first and/or second focusing lens(es).

When the measuring optical system repeatedly performs OCT to substantially the same cross section of the eye and a movie is displayed, the following may be applied. The display displays an image for position designation that is movable relatively to the movie according to a predetermined operation performed using the operation part. Based on a position designated by the operation to the image for position designation, the third target-position obtaining part may obtain the target position(s) of the first and/or second focusing lens(es).

The controller may display, as the image for position designation, an image indicating a position on the movie corresponding to a position of the second focusing lens during the repetitive OCT.

According to such an embodiment, a desired focus position(s) may be designated to a cross-sectional image, and a focus position(s) for eye photography and/or OCT may be adjusted to the designated position(s) automatically.

Fourth Embodiment

In order to optimize focus position for OCT in actual examinations, it is to be desired that not only differences between light wavelengths for photography (such as visible wavelengths) and those for OCT (such as near-infrared wavelengths) but also individual differences of optical properties of eyes are concerned. The present embodiment takes optical properties of eyes into account to perform focus adjustment for OCT. Such focus adjustment includes two steps, namely, rough adjustment and fine adjustment. Rough adjustment is performed using split target (focusing index) or measured value of eye refractive power. Fine adjustment is performed based on interference sensitivity of OCT.

[Configurations]

An ophthalmologic observation apparatus of the present embodiment has overall configuration and optical systems similar to the first embodiment. Control system is also almost the same as the first embodiment. In the following explanation, same symbols are used for components similar to those in the first embodiment.

Figure 11:
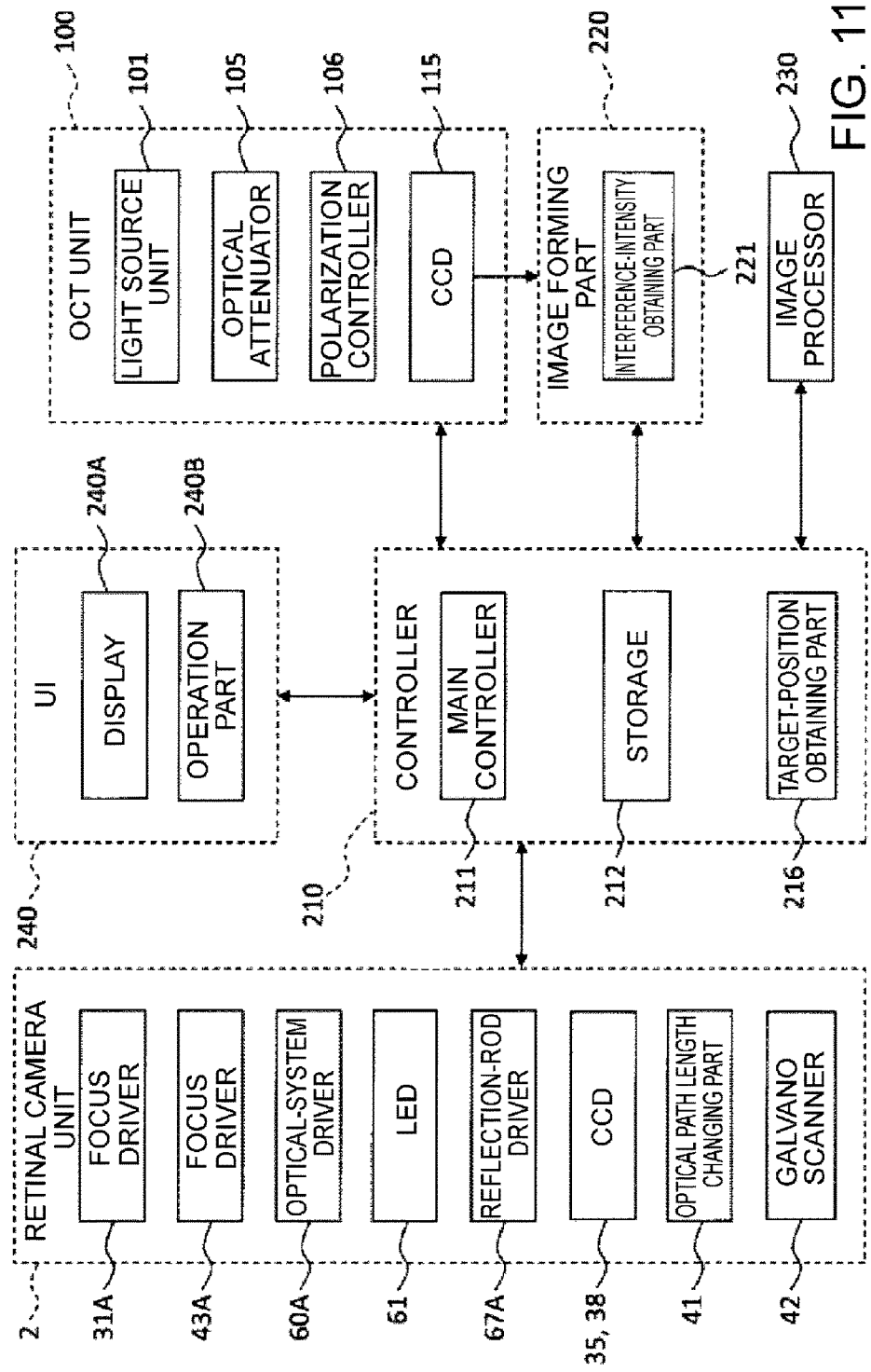
FIG. 11 is a schematic block diagram illustrating a configuration example of an ophthalmologic observation apparatus according to an embodiment.

FIG. 11 illustrates a configuration example of a control system of the ophthalmologic observation apparatus of the present embodiment. The controller 210 includes a target-position obtaining part 216. The image forming part 220 includes an interference-intensity obtaining part 221.

The interference-intensity obtaining part 221 obtains intensity of an interference signal (interference intensity) acquired by the measuring optical system that performs OCT. An interference signal is a detection signal output from the CCD 115 or a signal obtained by processing the detection signal. Examples of such signal processing include any signal processing used in Spectral Domain OCT or Swept Source OCT. The interference-intensity obtaining part 221 detects amplitude of an interference signal to obtain interference intensity, for example. The interference-intensity obtaining part 221 is an example of an "intensity obtaining part".

In the present embodiment, a plurality of interference signals are acquired while changing position of the focusing lens 43 in the measuring optical system. The interference-intensity obtaining part 221 obtains intensities of the respective interference signals. A plurality of interference signals is acquired in the following way, for example.

The main controller 211 controls the focus driver 43 to move the focusing lens 43. This movement may be continuous or discrete (stepwise). In the former case, the main controller 211 controls the measuring optical system (light source unit 101 etc.) to perform OCT multiple of times while continuously moving the focusing lens 43. In the latter case, the main controller 211 moves the focusing lens 43 to a 1st to nth positions successively and controls the measuring optical system to perform OCT in the state in which the focusing lens 43 is located at the respective positions. By performing such control, a plurality of interference signals corresponding to a plurality of locations of the focusing lens 43 is obtained.

In the above control, moving range of the focusing lens 43 may be set in advance. More specifically, a plurality of interference signals are acquired by performing OCT multiple of times while moving the focusing lens 43 within a preset range. The moving range of the focusing lens 43 includes a position predetermined by rough adjustment (focus adjustment on the basis of split target) described later. As an example, the center of the moving range of the focusing lens 43 is set to be located at the position (reference position) determined by rough adjustment. The moving range of the focusing lens 43 may be defined based on variation in refractive power with movement of the focusing lens 43 along the optical axis of the measuring optical system. As a specific example, the movement range of the focusing lens 43 is set to be a +/−3 diopters range centered at the reference position.

Based on the plurality of interference intensities obtained by the interference-intensity obtaining part 221, the target-position obtaining part 216 obtains a target position of the focusing lens 43. The target-position obtaining part 216 is an example of a "fourth target-position obtaining part".

An example of processing executed by the target-position obtaining part 216 is explained. The target-position obtaining part 216 specifies maximum intensity among the plurality of interference intensities obtained by the interference-intensity obtaining part 221. This processing is carried out by comparing values of the interference intensities. Further, the target-position obtaining part 216 sets a position of the focusing lens 43 corresponding to the specified maximum intensity as a target position. This processing is carried out by, for example: specifying a position when an interference signal with maximum intensity is acquired from among a plurality of positions of the focusing lens 43 applied to the plurality of OCT described above; and setting the specified position as a target position.

Processing executed by the target-position obtaining part 216 is not limited to this. For example, based on the plurality of interference intensities obtained, the target-position obtaining part 216 obtains variation in interference intensity with movement of the focusing lens 43. This processing includes finding a curve (continuous values) smoothly connecting values of the interference intensities (discrete values), for example. This curve may be defined in a coordinate system in which a horizontal axis indicates positions of the focusing lens 43 and vertical axis indicates interference intensities, for example. Further, the target-position obtaining part 216 finds a peak of interference intensity from the obtained variation in interference intensity. Then, the target-position obtaining part 216 obtains a position of the focusing lens 43 corresponding to the found peak. The obtained position may or may not be any of the plurality of positions of the focusing lens 43 applied to the plurality of OCT.

[Operations]

Figure 12:
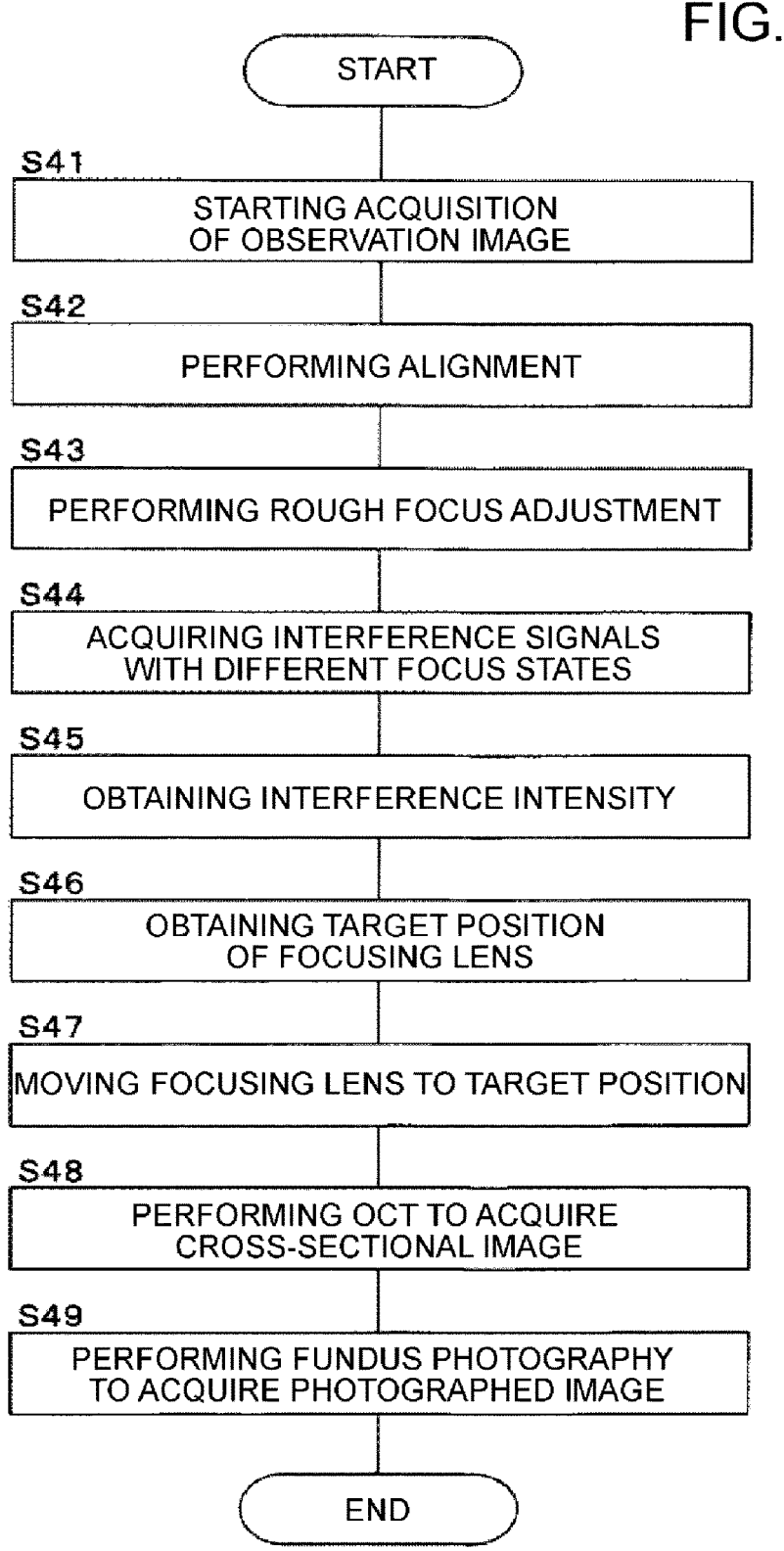
FIG. 12 is a flowchart representing an operation example of an ophthalmologic observation apparatus according to an embodiment.

Operations of the ophthalmologic observation apparatus of the present embodiment are described. FIG. 12 shows an example of an operation of the ophthalmologic observation apparatus.

(S41: Starting Acquisition of Observation Image)

As with the first embodiment, acquisition of observation image is commenced and fixation of the eye E is performed.

(S42: Performing Alignment)

Alignment target and split target are projected on the eye E as with the first embodiment. Then, alignment using the alignment target is carried out.

(S43: Performing Rough Focus Adjustment)

Focus adjustment using the split target (rough adjustment) is carried out. Rough adjustment may be performed manually or automatically (automatic focusing). Focus adjustment using the split target is described above.

Focus adjustment in this stage is performed for both the imaging optical system 30 and measuring optical system. For example, a position of the focusing lens 31 in the imaging optical system 30 is determined using the split target as with general retinal cameras, and the focusing lens 43 is moved to a position corresponding to the determined position. Here, relationship between positions of the focusing lens 31 and positions of the focusing lens 43 is determined in advance, and information indicating this relationship is stored in the storage 212.

(S44: Acquiring Interference Signals with Different Focus States)

The main controller 211 acquires a plurality of interference signals while changing the position of the focusing lens 43 in the measuring optical system. This processing is executed in the aforementioned way.

(S45: Obtaining Interference Intensity)

The interference-intensity obtaining part 221 obtains interference intensity of each of the plurality of interference signals acquired in Step 44.

(S46: Obtaining Target Position of Focusing Lens)

Based on the plurality of interference intensities obtained in Step 45, the target-position obtaining part 216 obtains a target position of the focusing lens 43.

(S47: Moving Focusing Lens to Target Position)

The main controller 211 controls the focus driver 43A to move the focusing lens 43 to the target position obtained in Step 46.

(S48: Performing OCT to Acquire Cross-Sectional Image)

The main controller 211 controls the OCT unit 100, optical-path-length changing part 41, galvano scanner 42, etc. to perform OCT of the fundus Ef. The image forming part 220 forms a cross-sectional image of the fundus Ef based on detection signals from the CCD 115. The main controller 211 displays the formed cross-sectional image on the display 240A. Further, the main controller 211 stores the formed cross-sectional image in the storage 212. Here, OCT is performed in a focus state finely adjusted based on interference intensity. Therefore, OCT with high sensitivity may be achieved.

(S49: Performing Fundus Photography to Acquire Photographed Image)

The main controller 211 controls the illumination optical system 10 (imaging light source 15 etc.) and imaging optical system 30 to acquire a photographed image of the fundus Ef. The main controller 211 displays the acquired photographed image on the display 240A. Further, the main controller 211 stores the acquired photographed image in the storage 212. This completes the present operation example. Here, this fundus photography is performed in a suitable focus state achieved by adjustment using split target in Step 43. This completes the present operation example.

[Actions and Effects]

Actions and effects of the ophthalmologic observation apparatus of the present embodiment are explained.

The ophthalmologic observation apparatus of the present embodiment includes a photographing optical system, measuring optical system, optical-path coupler, first and second drivers and controller. Consequently, the photographing optical system and measuring optical system have the respective individual focusing lenses, and these focusing lenses may be controlled individually. Therefore, the first focusing lens may be positioned at an optimal focus position for acquiring front images and the second focusing lens may be positioned at an optimal focus position for OCT. Therefore, it is possible to perform both front-image acquisition and OCT of the eye E with suitable focus conditions.

In the present embodiment, the measuring optical system performs OCT for acquiring a cross-sectional image of the fundus Ef. Further, the ophthalmologic observation apparatus of the present embodiment includes the focus optical system 60 (projecting optical system) and interference-intensity obtaining part 221 (intensity obtaining part). The projecting optical system projects, onto the fundus Ef, split target (focusing index) indicating a state of focus of the imaging optical system 30 on the fundus Ef. The interference-intensity obtaining part 221 obtains intensity of an interference signal acquired by the measuring optical system. Further, after focusing of the imaging optical system 30 and focusing of the measuring optical system are performed based on the focusing index (that is, after rough adjustment is performed), the main controller 211 controls the focus driver 43A based on the interference intensity obtained by the interference-intensity obtaining part 221 to perform fine adjustment of focus condition of the measuring optical system.

In the present embodiment, controller 210 may execute the following processing. The main controller 211 controls the measuring optical system while controlling the focus driver 43A to move the focusing lens 43 to acquire a plurality of interference signals corresponding to a plurality of positions of the focusing lens 43. Next, the target-position obtaining part 216 obtains a target position of the focusing lens 43 based on a plurality of interference intensities obtained by the interference-intensity obtaining part 221. Further, the main controller 211 controls the focus driver 43A so as to move the focusing lens 43 to the obtained target position.

The target-position obtaining part 216 specifies maximum intensity among the plurality of interference intensities obtained by the interference-intensity obtaining part 221, and adopts a position of the focusing lens 43 corresponding to the specified maximum intensity as the target position.

The main controller 211 moves the focusing lens 43 within a predetermined range to acquire the plurality of interference signals, thereby streamlining fine adjustment. This predetermined range may include the position of the focusing lens 43 determined by rough adjustment. In particular, the center of the predetermined range may be located at the position of the focusing lens 43 determined by rough adjustment.

Rough adjustment is performed manually or automatically. In the automatic case, the ophthalmologic observation apparatus of the present embodiment may be configured as follows. The imaging optical system 30 includes an infrared photographing optical system that uses infrared light to perform photography for acquiring a front image of the fundus Ef. The infrared photographing optical system may be the optical system that illuminates the eye E with observation illumination light and detects its returned light described in the first embodiment. The main controller 211 performs focusing of the imaging optical system 30 by moving the focusing lens 31 and focus optical system 60 based on the front image acquired by photographing, using the infrared photographing optical system, the fundus Ef on which the split target is projected, and based on the result of this focusing, performs focusing of the measuring optical system (that is, movement of the focusing lens 43).

Such an embodiment is capable of performing OCT with high sensitivity because focus conditions of the measuring optical system may be adjusted based on interference intensity. For example, OCT may be performed with suitable focus condition even when rough adjustment cannot be performed properly due to vignetting of split target by an iris. Further, fine adjustment may be commenced smoothly because rough adjustment is performed prior to fine adjustment.

Modification Examples

Modification examples of the present embodiment are explained.

Rough adjustment may be performed using a measured value of refractive power of the eye E obtained in advance instead of using split target. A configuration of the present modification example may be the same as the fourth embodiment (see FIG. 11) unless otherwise stated.

The storage 212 stores a measured value of refractive power of the eye E obtained in advance. The measured value may be obtained by other ophthalmologic apparatus (automatic refractometer etc.) or this ophthalmologic observation apparatus. In the former case, the main controller 211 stores a measured value input to this ophthalmologic observation apparatus into the storage 212. In the latter case, this ophthalmologic observation apparatus is provided with a refractive-power obtaining part that obtains refractive power of an eye to be examined. The refractive-power obtaining part includes configurations described in the first embodiment, for example. The main controller 211 stores a measured value obtained by the refractive-power obtaining part into the storage 212.

The interference-intensity obtaining part 221 obtains intensity of the interference signal acquired by the measuring optical system as with the above embodiment. As rough focus adjustment, the main controller 211 performs focus adjustments of the imaging optical system 30 and measuring optical system on the basis of the measured value stored in the storage 212. Focus adjustment on the basis of eye refractive power is performed in the same manner as the first embodiment, for example. Further, the main controller 211 controls the focus driver 43A based on the interference intensity obtained by the interference-intensity obtaining part 221 to perform fine adjustment of focus condition of the measuring optical system.

The present modification example is capable of performing OCT with high sensitivity because focus conditions of the measuring optical system may be adjusted based on interference intensity. Further, fine adjustment may be commenced smoothly because rough adjustment is performed prior to fine adjustment. Moreover, even if an ophthalmologic observation apparatus does not have a function of projecting a focusing index such as a split target or even when such a function has trouble, rough adjustment of focus conditions may be performed.

Modification Examples

The configurations described above are merely illustrations for favorably implementing the present invention. Therefore, it is possible to make arbitrary modifications (omission, replacement, addition, etc.) within the scope of the present invention. Further, various configurations described in the above embodiments may be combined in arbitrary ways.

In the above embodiments, the optical-path-length difference between optical paths of the signal light LS and reference light LR is changed by varying the position of the optical-path-length changing part 41; however, methods for changing the optical-path-length difference are not limited to this. For example, the optical-path-length difference may be changed by providing a reflection mirror (reference mirror) in the optical path of the reference light and moving the reference mirror in the advancing direction of the reference light to change the optical path length of the reference light. Further, the optical-path-length difference may be changed by moving the retinal camera unit 2 and/or OCT unit 100 relatively to the eye E to change the optical path length of the signal light LS. When an object is not a site of a living body or the like, the optical-path-length difference may be changed by moving the object in the depth direction (z-direction).

Computer programs for implementing the above embodiments may be stored in any kinds of computer-readable recording media. Examples of such recording media include an optical disk, semiconductor memory, magneto-optic disk (CD-ROM, DVD-RAM, DVD-ROM, MO, etc.), magnetic storage (a hard disk, a floppy disk (TM), ZIP, etc.), etc.

The programs may be transmitted through networks such as internet, LAN, etc.

What is claimed is:

1. An ophthalmologic observation apparatus comprising:
a photographing optical system that includes a first focusing lens and performs photography for acquiring a front image of an eye;
a measuring optical system that includes a second focusing lens and performs optical coherence tomography (OCT) for acquiring a cross-sectional image of the eye;
an optical-path coupler that couples optical paths of the photographing optical system and the measuring optical system at a location on the eye side than the first and second focusing lenses, wherein the optical-path coupler is disposed between the first focusing lens and the eye and the optical-path coupler is disposed between the second focusing lens and the eye;
a first driver for moving the first focusing lens along an optical axis of the photographing optical system;
a second driver for moving the second focusing lens along an optical axis of the measuring optical system;
a display that displays a cross-sectional image acquired by OCT performed by the measuring optical system;
an operation part for designating a position in the displayed cross-sectional image; and
a controller that controls the first and second drivers individually, wherein
the photographing optical system performs photography for acquiring a front image of a fundus of the eye, and
the measuring optical system performs OCT for acquiring a cross-sectional image of the fundus of the eye,
further comprising a refractive-power obtaining part that obtains refractive power of the eye, wherein
the controller includes:
a first target-position obtaining part that obtains a target position of the second focusing lens of the measuring optical system based on the obtained refractive power and controls the second driver so as to move the second focusing lens to the obtained target position, wherein the first target-position obtaining part further obtains a target position of the first focusing lens based on the obtained target position to which the second focusing lens is moved;
a storage that stores in advance:
first association information in which values of eye refractive power and positions of the first focusing lens are associated; and
second association information in which values of eye refractive power and positions of the second focusing lens are associated; and
the first target-position obtaining part obtains target positions of the first and second focusing lenses based on the refractive power obtained by the refractive-power obtaining part and the first and second association information, and wherein each of the first association information and the second association information comprises at least one of:
information in which discrete values are associated with each other; and
information in which continuous values are associated with each other; and wherein
the controller includes a third target-position obtaining part that obtains a target position of the first focusing lens and/or a target position of the second focusing lens based on the position designated using the operation part, and controls the first driver and/or the second driver so as to move the first focusing lens to the obtained target position and/or move the second focusing lens to the obtained target position;
the measuring optical system repeatedly performs OCT to substantially the same cross section of the eye;
the display displays a plurality of cross-sectional images acquired by the repetitive OCT as a movie;
the controller switches this movie display to still-image display in response to a predetermined operation performed using the operation part; and
the third target-position obtaining part obtains the target position based on a position designated to a cross-sectional image displayed as a still image using the operation part.

2. The ophthalmologic observation apparatus of claim 1, wherein
the photographing optical system includes an infrared photographing optical system that uses infrared light to perform photography of the fundus, and
the refractive-power obtaining part includes:
a projecting optical system that projects, onto the fundus, a focusing index indicating a state of focus of the photographing optical system on the fundus; and
an analyzer that analyzes a front image acquired by photographing the fundus on which the focusing index is projected by means of the infrared photographing optical system to obtain refractive power of the eye.

3. The ophthalmologic observation apparatus of claim 1, wherein the controller includes a second target-position obtaining part that obtains a target position of the first focusing lens based on the position of the second focusing lens when the measuring optical system has performed OCT, and controls the first driver so as to move the first focusing lens to the obtained target position.

4. The ophthalmologic observation apparatus of claim 3, wherein
the measuring optical system repeatedly performs OCT to substantially the same cross section of the eye, and
the second target-position obtaining part obtains a target position of the first focusing lens on the basis of the position of the second focusing lens set based on a plurality of cross-sectional images acquired by the repetitive OCT.

5. An ophthalmologic observation apparatus comprising:
a photographing optical system that includes a first focusing lens and performs photography for acquiring a front image of an eye;
a measuring optical system that includes a second focusing lens and performs optical coherence tomography (OCT) for acquiring a cross-sectional image of the eye;
an optical-path coupler that couples optical paths of the photographing optical system and the measuring optical system at a location on the eye side than the first and second focusing lenses, wherein the optical-path coupler is disposed between the first focusing lens and the eye and the optical-path coupler is disposed between the second focusing lens and the eye;
a first driver for moving the first focusing lens along an optical axis of the photographing optical system;
a second driver for moving the second focusing lens along an optical axis of the measuring optical system;
a display that displays a cross-sectional image acquired by OCT performed by the measuring optical system;
an operation part for designating a position in the displayed cross-sectional image; and
a controller that controls the first and second drivers individually, wherein
the photographing optical system performs photography for acquiring a front image of a fundus of the eye, and
the measuring optical system performs OCT for acquiring a cross-sectional image of the fundus of the eye,
further comprising a refractive-power obtaining part that obtains refractive power of the eye, wherein
the controller includes:
a first target-position obtaining part that obtains a target position of the a target position of the second focusing lens of the measuring optical system based on the obtained refractive power and controls the second driver so as to move the second focusing lens to the obtained target position, wherein the first target-position obtaining part further obtains a target position of the first focusing lens based on the obtained target position to which the second focusing lens is moved;
a storage that stores in advance:
first association information in which values of eye refractive power and positions of the first focusing lens are associated; and
second association information in which values of eye refractive power and positions of the second focusing lens are associated; and
the first target-position obtaining part obtains target positions of the first and second focusing lenses based on the refractive power obtained by the refractive-power obtaining part and the first and second association information, and
wherein each of the first association information and the second association information comprises at least one of:
information in which discrete values are associated with each other; and
information in which continuous values are associated with each other; and wherein
the controller includes a third target-position obtaining part that obtains a target position of the first focusing lens and/or a target position of the second focusing lens based on the position designated using the operation part, and controls the first driver and/or the second driver so as to move the first focusing lens to the obtained target position and/or move the second focusing lens to the obtained target position;
wherein
the measuring optical system repeatedly performs OCT to substantially the same cross section of the eye,
the display displays a plurality of cross-sectional images acquired by the repetitive OCT as a movie and displays an image for position designation that is movable relatively to the movie according to a predetermined operation performed using the operation part, and
the third target-position obtaining part obtains the target position based on a position designated by the operation to the image for position designation.

6. The ophthalmologic observation apparatus of claim 5, wherein the controller displays the image for position designation indicating a position on the movie corresponding to the position of the second focusing lens during the repetitive OCT.

7. The ophthalmologic observation apparatus of claim 1, further comprising a layer-region specifying part that analyzes a cross-sectional image displayed on the display to specify a layer region in the cross-sectional image corresponding to a predetermined layer, wherein
the display displays a layer image indicating the specified layer region over the cross-sectional image.

8. The ophthalmologic observation apparatus of claim 1, wherein
the measuring optical system performs OCT for acquiring a cross-sectional image of a fundus of the eye, further comprising:
a projecting optical system that projects, onto the fundus, a focusing index indicating a state of focus of the photographing optical system on the fundus; and
an intensity obtaining part that obtains intensity of an interference signal acquired by the measuring optical system, wherein
after focusing of the photographing optical system and focusing of the measuring optical system are performed based on the focusing index, the controller controls the second driver based on the intensity obtained by the intensity obtaining part.

9. The ophthalmologic observation apparatus of claim 8, wherein the controller acquires a plurality of interference signals corresponding to a plurality of positions of the second focusing lens by controlling the measuring optical system while controlling the second driver to move the second focusing lens, includes a fourth target-position obtaining part that obtains a target position of the second focusing lens based on intensities of the plurality of interference signals obtained by the intensity obtaining part, and controls the second driver so as to move the second focusing lens to the obtained target position.

10. The ophthalmologic observation apparatus of claim 9, wherein the fourth target-position obtaining part specifies maximum intensity among the intensities of the plurality of interference signals, and sets a position of the second focusing lens corresponding to the specified maximum intensity as the target position.

11. The ophthalmologic observation apparatus of claim 9, wherein the controller moves the second focusing lens within a predetermined range to acquire the plurality of interference signals.

12. The ophthalmologic observation apparatus of claim 11, wherein the predetermined range includes a position of the second focusing lens determined based on the focusing index in advance.

13. The ophthalmologic observation apparatus of claim 12, wherein the center of the predetermined range is located at the position determined in advance.

14. The ophthalmologic observation apparatus of any of claim 8, further comprising an infrared photographing optical system that uses infrared light to perform photography for acquiring a front image of a fundus of the eye, wherein
the controller performs focusing of the photographing optical system by moving the first focusing lens and the projecting optical system based on the front image acquired by photographing the fundus on which the focusing index is projected by means of the infrared photographing optical system, and based on the result of this focusing, performs focusing of the measuring optical system.

15. The ophthalmologic observation apparatus of claim 1, wherein the measuring optical system performs OCT for acquiring a cross-sectional image of a fundus of the eye, further comprising:

a storage that stores a measured value of refractive power of the eye obtained in advance; and an intensity obtaining part that obtains intensity of an interference signal acquired by the measuring optical system, wherein after focusing of the photographing optical system and focusing of the measuring optical system are performed based on the measured value, the controller controls the second driver based on the intensity obtained by the intensity obtaining part.

16. The ophthalmologic observation apparatus of claim 15, further comprising a refractive-power obtaining part that obtains refractive power of the eye, wherein the controller stores the obtained refractive power as the measured value in the storage.

* * * * *